United States Patent
Oh et al.

(10) Patent No.: US 10,376,553 B2
(45) Date of Patent: Aug. 13, 2019

(54) **PHARMACEUTICAL COMPOSITION FOR PREVENTING AND TREATING CHRONIC OBSTRUCTIVE LUNG DISEASE CONTAINING, AS ACTIVE INGREDIENT, *MAGNOLIAE FLOS* EXTRACT, FRACTION, OR ACTIVE FRACTION THEREOF**

(71) Applicant: KOREA RESEARCH INSTITUTE OF BIOSCIENCE AND BIOTECHNOLOGY, Daejeon (KR)

(72) Inventors: Sei-Ryang Oh, Daejeon (KR); Kyung Seop Ahn, Daejeon (KR); Su Ui Lee, Daejeon (KR); Hyung Won Ryu, Daejeon (KR); Doo-Young Kim, Daejeon (KR); Hyeong Kyu Lee, Daejeon (KR); Ok-Kyoung Kwon, Daejeon (KR); Jung Hee Kim, Daejeon (KR); Hyun-Jun Lee, Daejeon (KR); In-Sik Shin, Gwangju (KR)

(73) Assignee: KOREA RESEARCH INSTITUTE OF BIOSCIENCE AND BIOTECHNOLOGY, Daejeon (KR)

( * ) Notice: Subject to any disclaimer, the term of this patent is extended or adjusted under 35 U.S.C. 154(b) by 0 days.

(21) Appl. No.: 15/573,207

(22) PCT Filed: May 13, 2016

(86) PCT No.: PCT/KR2016/005113
§ 371 (c)(1),
(2) Date: Nov. 10, 2017

(87) PCT Pub. No.: WO2016/182399
PCT Pub. Date: Nov. 17, 2016

(65) Prior Publication Data
US 2018/0353561 A1    Dec. 13, 2018

(30) Foreign Application Priority Data
May 13, 2015    (KR) .................. 10-2015-0066621

(51) Int. Cl.
*A61K 36/575* (2006.01)
*A61P 11/00* (2006.01)
(Continued)

(52) U.S. Cl.
CPC ............ *A61K 36/575* (2013.01); *A61K 31/34* (2013.01); *A61K 31/357* (2013.01); *A61K 31/36* (2013.01);
(Continued)

(58) Field of Classification Search
CPC .................................................... A61K 36/575
See application file for complete search history.

(56) References Cited

U.S. PATENT DOCUMENTS

2007/0231403 A1* 10/2007 Park ...................... A61K 36/14
424/539

FOREIGN PATENT DOCUMENTS

CN    101530472 A    9/2009
CN    102370593 A    3/2012
(Continued)

OTHER PUBLICATIONS

Tiffany Coon et al., "Novel PDE4 Inhibitors Derived from Chinese Medicine Forsythia", PLOS ONE, Dec. 30, 2014, 14 pages, vol. 9, No. 12.
(Continued)

*Primary Examiner* — Rosanne Kosson
(74) *Attorney, Agent, or Firm* — Sughrue Mion, PLLC

(57) ABSTRACT

A pharmaceutical composition includes any of an extract of *Magnoliae flos*, a fraction or an active fraction obtained by fractionation thereof with an organic solvent, and a compound separated therefrom as an active ingredient. The extract of *Magnoliae flos*, the fraction or the active fraction obtained by fractionation thereof with an organic solvent, or the compound separated therefrom inhibits the expression of MUC5AC induced by TNF-α and the promoter activity in human lung cancer mucosal cells (H292), reduces the num-
(Continued)

ber of inflammatory cells in the bronchoalveolar lavage fluid of the chronic obstructive pulmonary disease mouse model, inhibits the production of reactive oxygen species, and reduces the cytokines; and therefore are effective in preventing or treating chronic obstructive pulmonary disease.

11 Claims, 10 Drawing Sheets

(51) Int. Cl.
    *A61K 31/34*     (2006.01)
    *A61K 31/36*     (2006.01)
    *A61P 9/00*     (2006.01)
    *A61P 35/00*     (2006.01)
    *A61K 31/357*     (2006.01)
    *A61K 9/00*     (2006.01)
    *A61K 47/38*     (2006.01)

(52) U.S. Cl.
    CPC ............... *A61P 9/00* (2018.01); *A61P 11/00* (2018.01); *A61P 35/00* (2018.01); *A61K 9/0019* (2013.01); *A61K 9/0095* (2013.01); *A61K 47/38* (2013.01)

(56) References Cited

FOREIGN PATENT DOCUMENTS

| | | |
|---|---|---|
| CN | 104398503 A | 3/2015 |
| JP | 665224 A | 3/1994 |
| KR | 100321313 B1 | 8/2002 |
| KR | 10-2011-0036317 A | 4/2011 |
| KR | 10-2015-0031780 | 3/2015 |

OTHER PUBLICATIONS

Jin Ah Baek et al., "Extracts of Magnoliae flos inhibit inductible nitric oxide synthase via ERK in human respiratory epithelial cells", Mar. 1, 2009, pp. 122-128, vol. 20, Issue 2.
International Search Report for PCT/KR2016/005113 dated Oct. 25, 2016 [PCT/ISA/210].
European Patent Office: Communication dated Jan. 8, 2019 in application No. 16793045.2.
Database WPI, Week 201114, 2011, Thomson Scientific, London, GB; AN 2011-P56917 XP002786566, 5 pages.
Kong, C-S., et al., "In Vitro Evaluation on the Antiobesity Effect of Lignans from the Flower Buds of *Magnolia denudata*", Journal of Agricultural and Food Chemistry, 2011, vol. 59, No. 10, XP055523927, pp. 5665-5670.
Shen, Y., et al., "Chemistry and Bioactivity of *Flos Magnoliae*, A Chinese Herd for Rhinitis and Sinusitis", Current Medicinal Chemistry, 2008, vol. 15, No. 16, XP009146566, pp. 1616-1627.
Usery, et al., "Potential Role of Leukotriene Modifiers in the Treatment of Chronic Obstructive Pulmonary Disease", Pharmacotherapy, vol. 28, No. 9, 2008, 1183-1187 (6 pages total).
Japanese Patent Office; Communication dated Oct. 9, 2018, in counterpart application No. 2017-559060.
Simon Gompertz et al., "A Randomized, Placebo-Controlled Trial of a Leukotriene Synthesis Inhibitor in Patients With COPD", Chest, vol. 122, No. 1, pp. 289-294, Jul. 2002, 7 pages total.

* cited by examiner

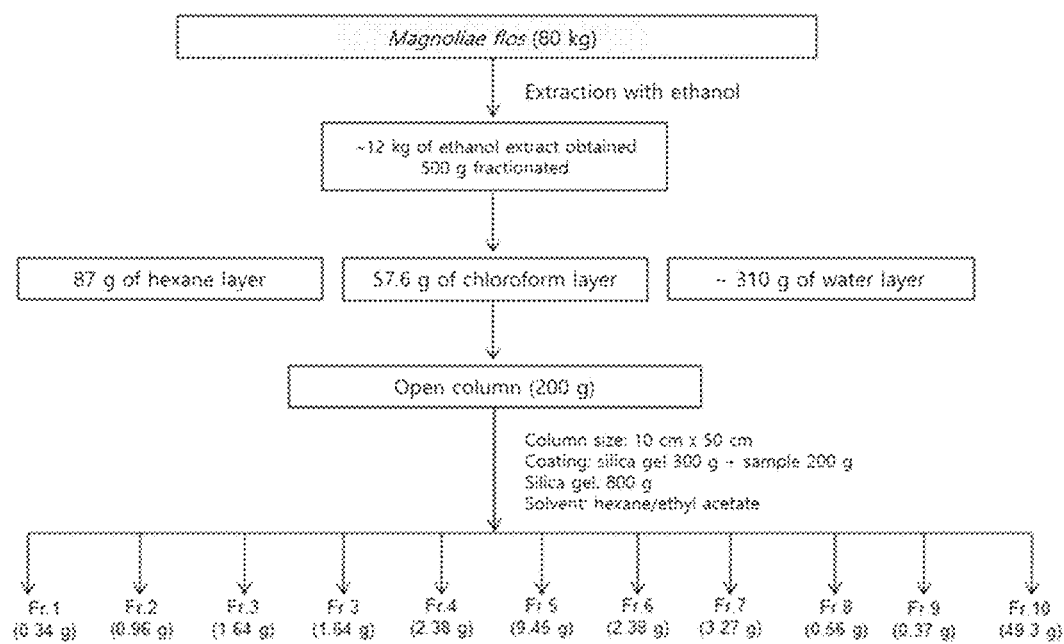
[Fig. 1]

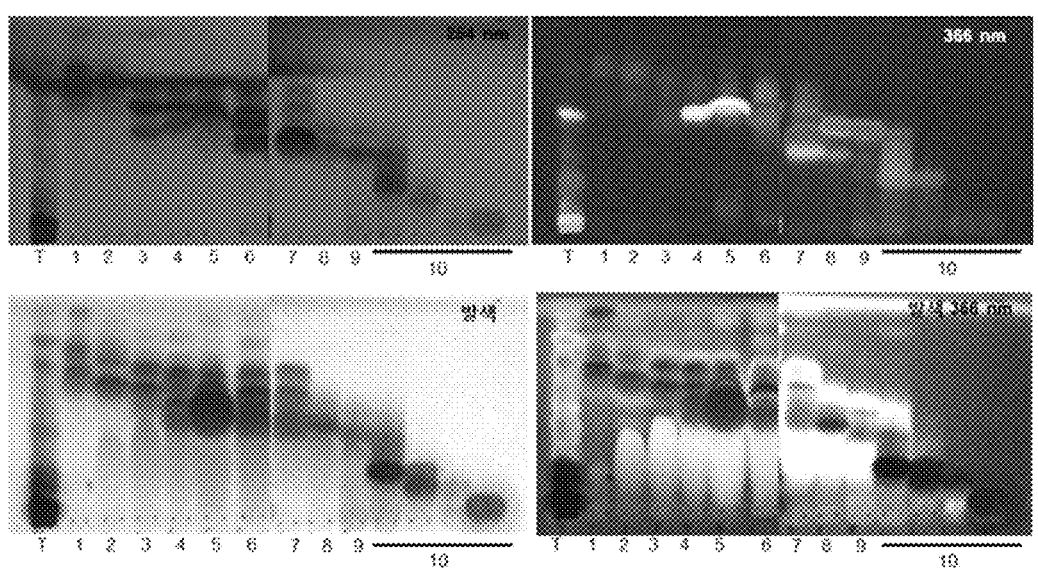
[Fig. 2]
Thin layer chromatography (Magnoliae flos extract and fractions) – hexane/ethyl acetate = 3:1

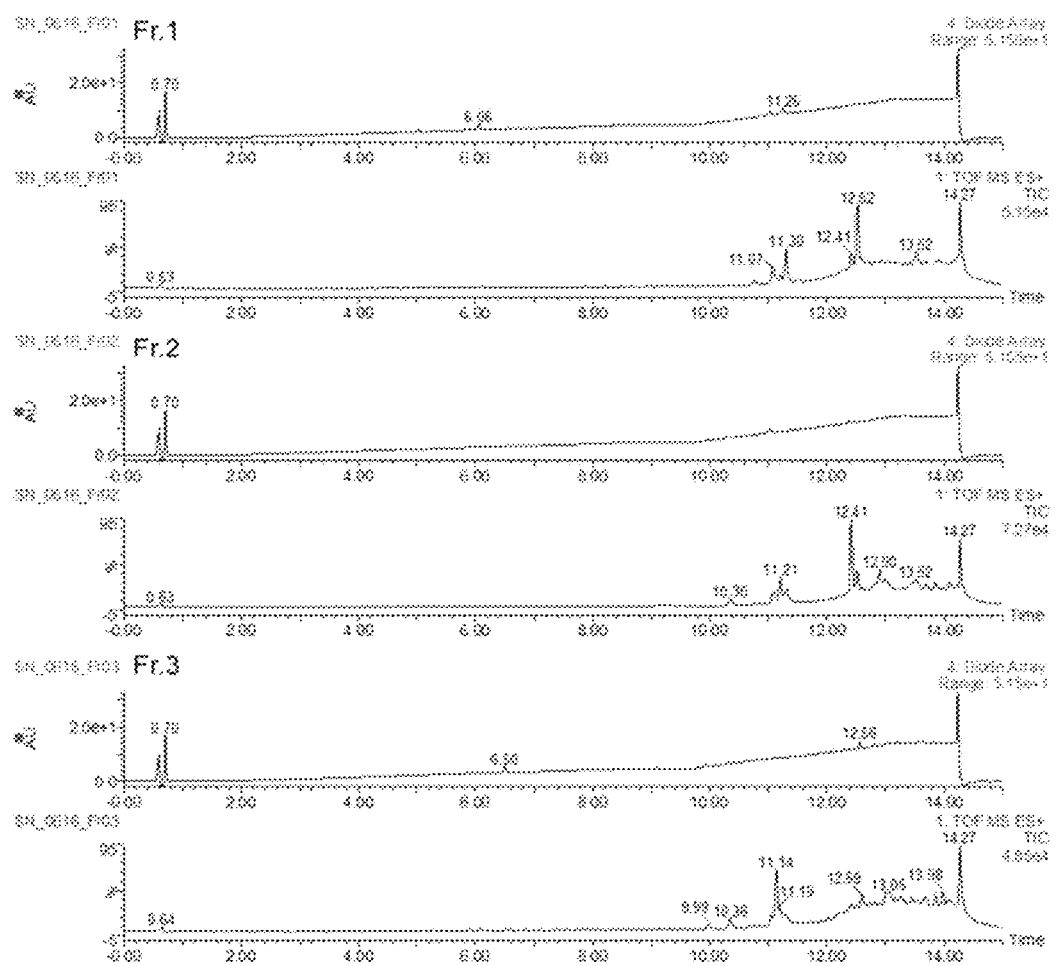
[Fig. 3a]

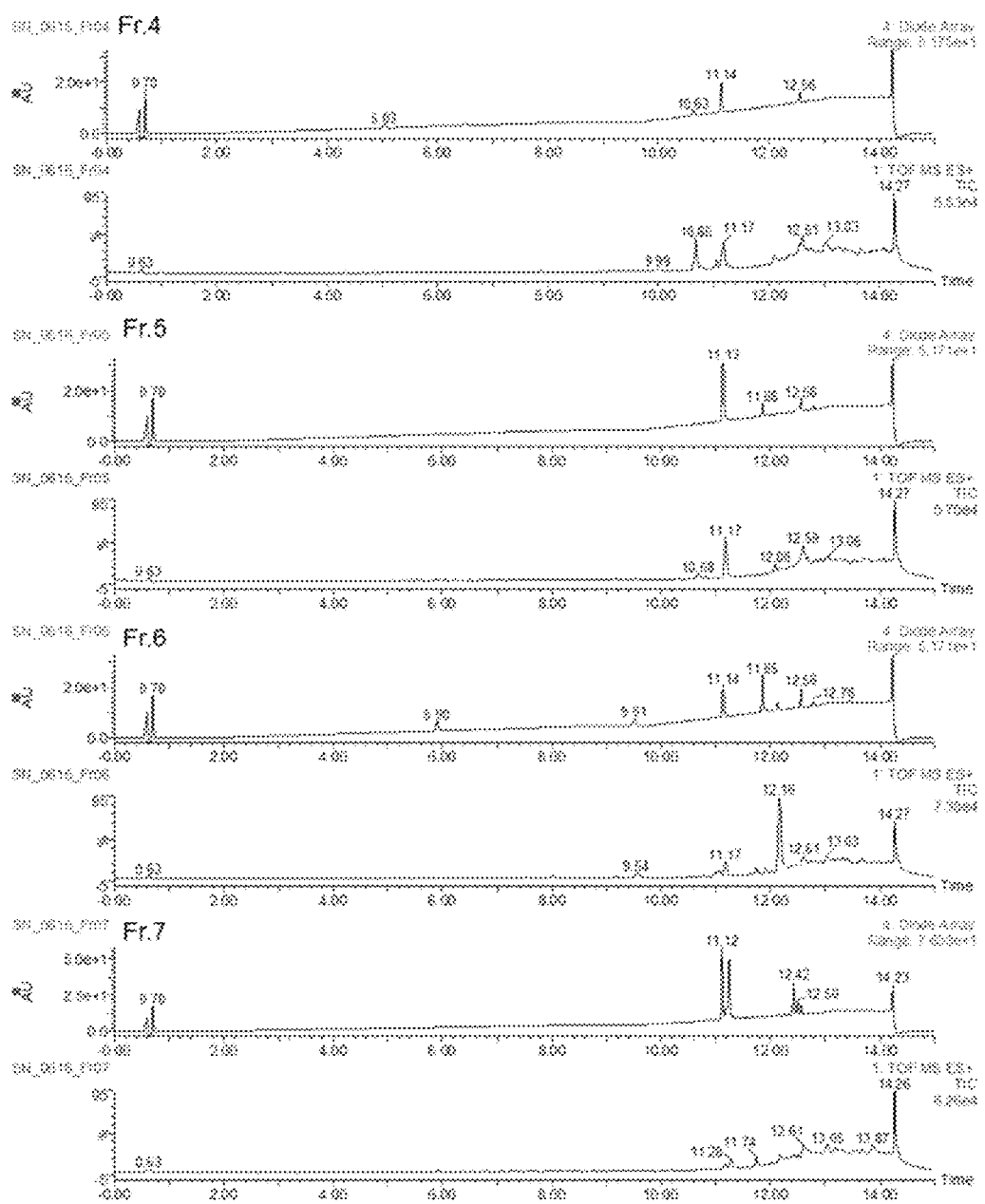
[Fig. 3b]

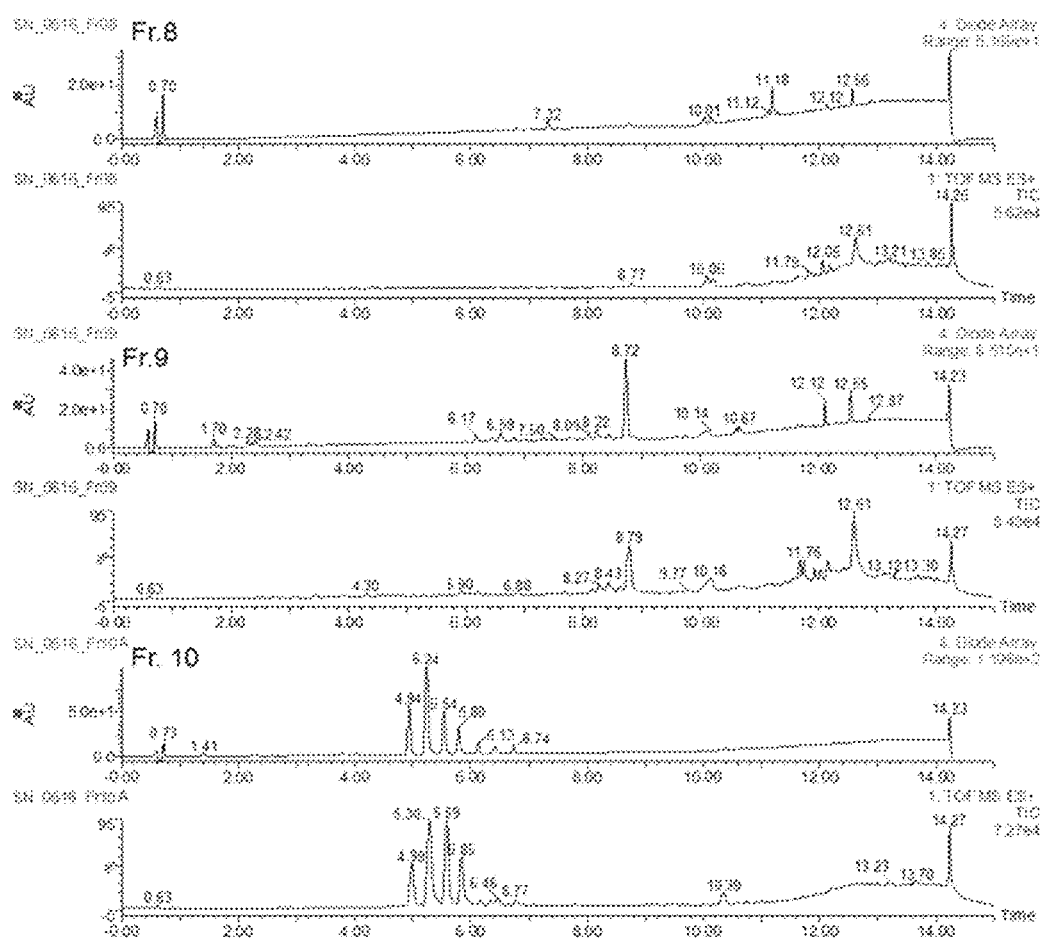
[Fig. 3c]

[Fig. 4a]
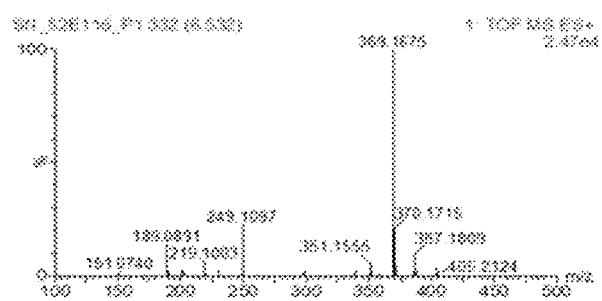
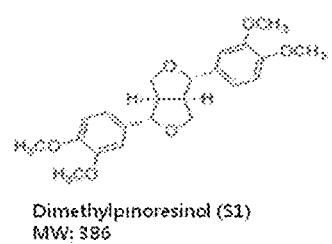
Dimethylpinoresinol (S1)
MW: 386
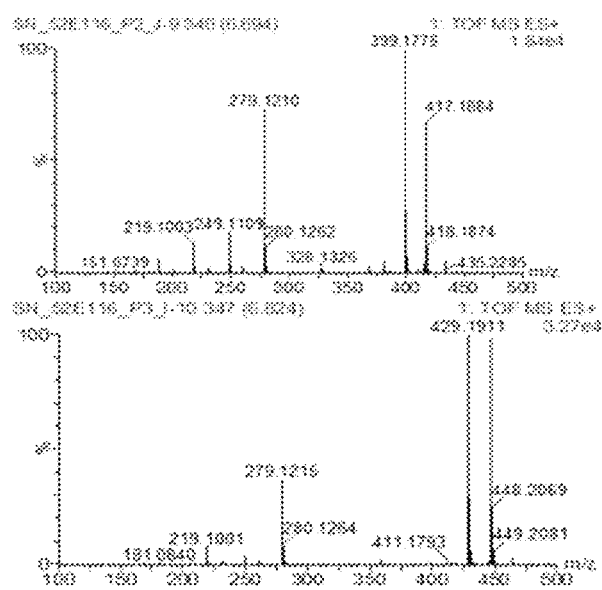
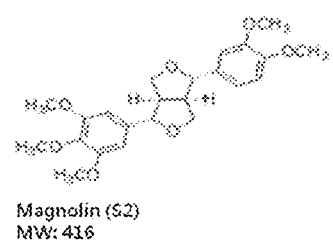
Magnolin (S2)
MW: 416
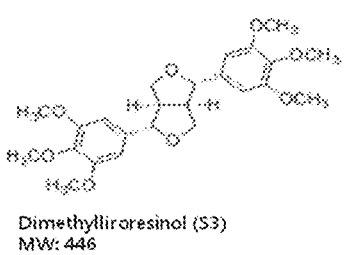
Dimethyliiroresinol (S3)
MW: 446

[Fig. 4b]
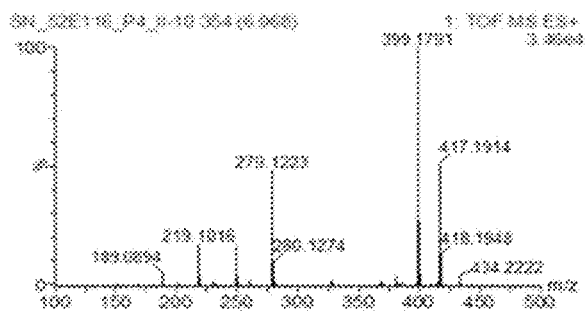
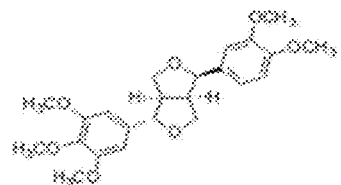
Epimagnolin (S4)
MW: 416
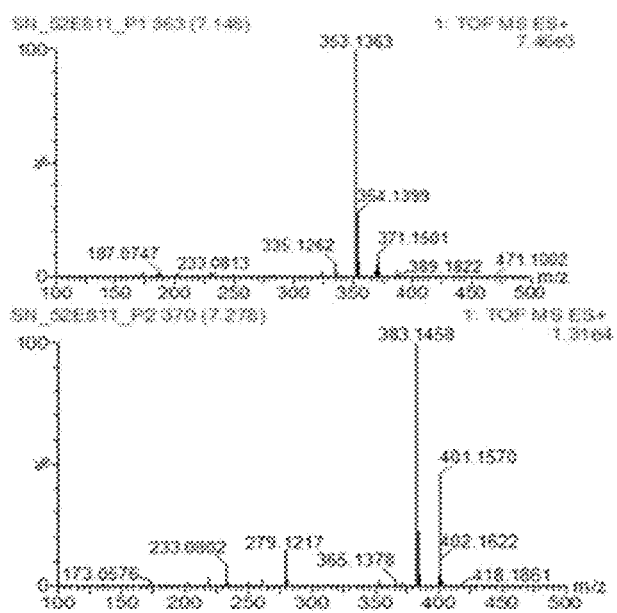
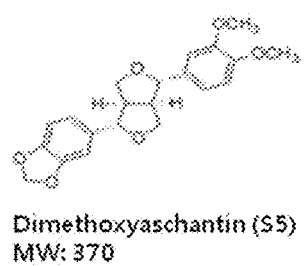
Dimethoxyaschantin (S5)
MW: 370
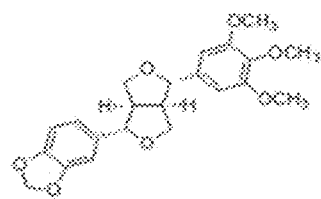
Aschantin (S6)
MW: 400
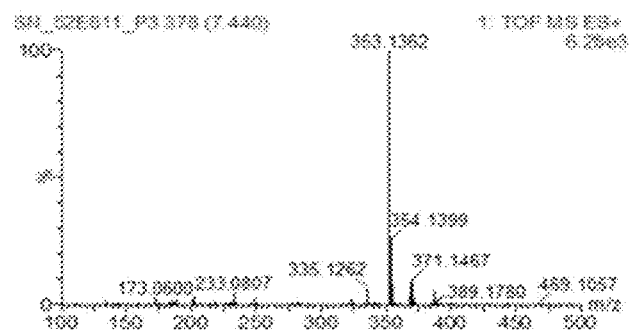
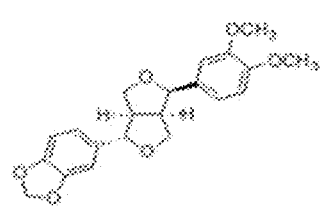
Fargesin (S7)
MW: 370

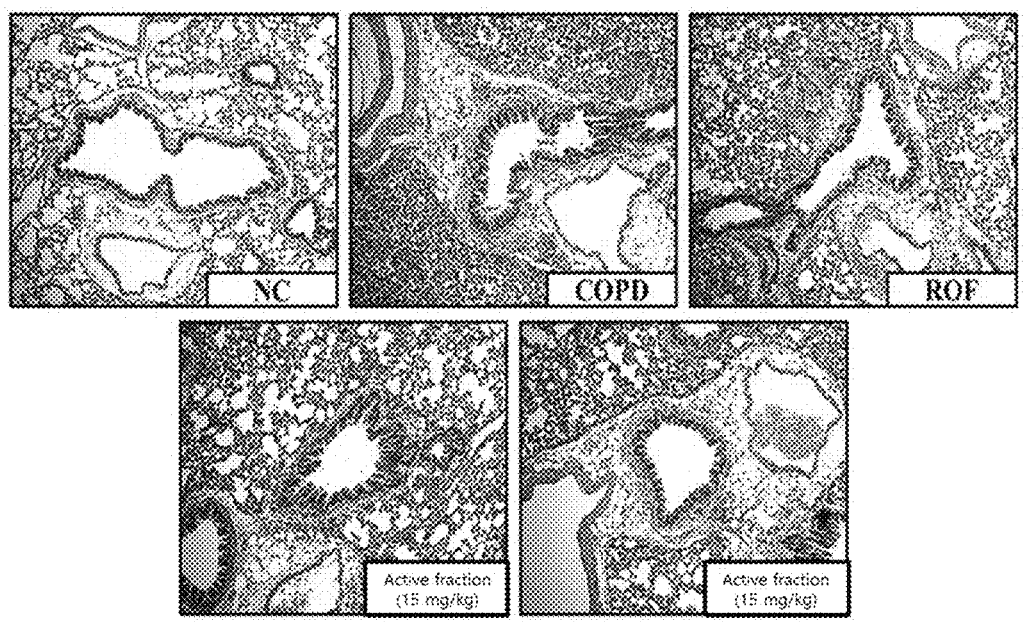
[Fig. 5a]

[Fig. 5b]
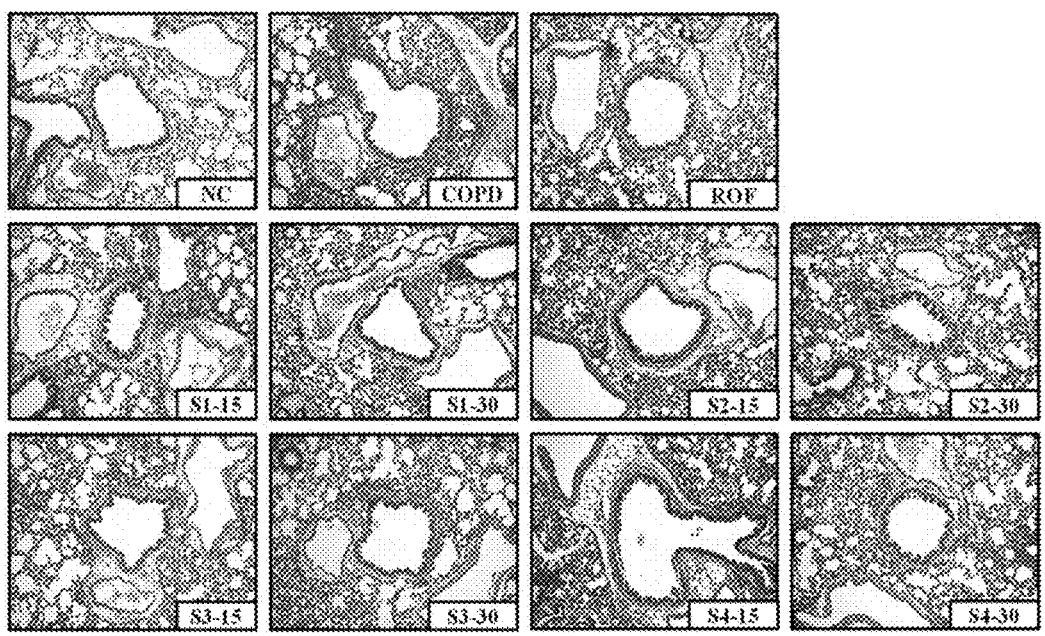

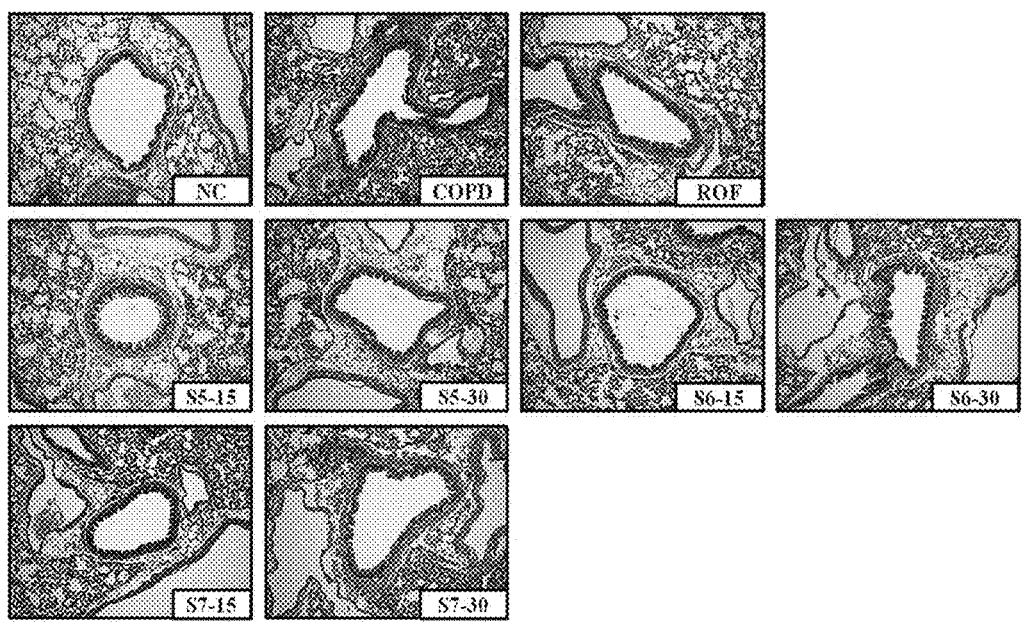
[Fig. 5c]

PHARMACEUTICAL COMPOSITION FOR PREVENTING AND TREATING CHRONIC OBSTRUCTIVE LUNG DISEASE CONTAINING, AS ACTIVE INGREDIENT, *MAGNOLIAE FLOS* EXTRACT, FRACTION, OR ACTIVE FRACTION THEREOF

CROSS REFERENCE TO RELATED APPLICATIONS

This application is a National Stage of International Application No. PCT/KR2016/005113 filed May 13, 2016, claiming priority based on Korean Patent Application No. 10-2015-0066621 filed May 13, 2015, the contents of all of which are incorporated herein by reference in their entirety.

TECHNICAL FIELD

The present invention relates to the use of an extract of *Magnoliae flos*, a fraction or an active fraction obtained by fractionation thereof with an organic solvent, or a compound separated therefrom, and specifically to a pharmaceutical composition comprising any of the extract of *Magnoliae flos*, the fraction or the active fraction obtained by fractionation thereof with an organic solvent, and the compound separated therefrom as an active ingredient for preventing and treating chronic obstructive pulmonary disease.

BACKGROUND ART

Chronic obstructive pulmonary disease (COPD), a representative lung disease, differs from asthma in that it is associated with irreversible airway obstruction. Currently, chronic obstructive pulmonary disease is a major cause of death in many countries; especially, it is predicted to be the third cause of death in humans in 2020 (Vestbo et al., 2013). COPD is a disease caused by pathologic changes of the bronchi and lung parenchyma due to inflammation in the airway and pulmonary parenchymal. COPD is characterized by bronchiolitis obliterans and emphysema (pulmonary parenchymal destruction), and it persistently inhibits and closes airflow in the lung tissue, eventually leading to death of a patient (Le et al., 2009). Types of chronic obstructive pulmonary disease include chronic obstructive bronchitis, chronic bronchiolitis, and emphysema. Such chronic obstructive pulmonary disease is caused by various causes such as cigarette smoke, dust, chemicals, air pollution, and bacterial infection (Li et al., 2012).

In particular, smoking is considered to be the major cause of chronic obstructive pulmonary disease, and over 80% of patients with actual chronic obstructive pulmonary disease are smokers (Rabe et al., 2007). Cigarette smoke contains a number of toxic chemicals, causing harmful changes in the lung tissue upon smoking (Stampfli and Anderson, 2009). These toxic chemicals cause infiltration of various inflammatory cells including neutrophils in the lung tissue, resulting in pulmonary inflammation (Terashima et al., 1997). Clinical studies have also shown a significant increase in the number of neutrophils and macrophages in the bronchoalveolar lavage fluid (BALF) or sputum in patients with chronic obstructive pulmonary disease (O'Donnell et al., 2006). These inflammatory cells produce reactive oxygen species, inflammatory cytokines, chemokines, and a variety of enzymes that cause tissue damage (Profita et al., 2010). In particular, neutrophils play an important role in the development of chronic obstructive pulmonary disease (Hiemstra et al., 1998). Neutrophils not only produce many inflammatory cytokines, chemokines, and chemotactic factors, but also secrete elastinase, thereby destroying normal alveolar forms and eventually causing emphysema (Hoenderdos and Condliffe, 2013). Therefore, inhibition of infiltration of inflammatory cells, especially neutrophils, caused by cigarette smoke is recognized as an important therapeutic tool in the treatment of chronic obstructive pulmonary disease.

Airway mucus secretion is an innate immune response essential for the protection of airway mucosal surfaces from external pathogens (bacteria, viruses, and fungi) and stimuli (Voynow et al., 2009). However, excessive secretion and overproduction of airway mucus is a major pathophysiological feature of chronic obstructive pulmonary disease (COPD) (Rogers et al., 2006). Inhibition of excessive secretion and overproduction of airway mucus can be a primary strategy for the treatment of chronic obstructive pulmonary disease.

MUC5AC, one of the genes involved in the mucus secretion of mucin, is considered to be an important target factor because of the marked increase in its expression in COPD patients (Caramora et al., 2004). Expression of MUC5AC has been reported to be regulated by TNF-$\alpha$, a major cytokine that causes COPD (Matera et al., 2010). Indeed, animal models with overexpression of TNF-$\alpha$ show pathological features of COPD, such as cell inflow into the lung, bronchial injury, and emphysema (Lundblad et al., 2005). Therefore, the expression and production of MUC5AC is an important factor for elucidating the mechanism of chronic obstructive pulmonary disease, and researches for preventing or treating this disease are actively conducted through a search of drugs inhibiting it.

*Magnoliae flos* is a word that refers to the buds of magnolia flowers belonging to Magnoliaceae, and the flower buds taste a little bit spicy. Magnolia is a tall deciduous tree cultivated nationwide for the purpose of gardening. Its flowers bloom earlier than leaves, and the flowering period is from March to April. *Magnoliae flos* is considered to be warm by nature in the oriental medicine. It is also regarded as effective for headache, back pain, and rhinitis, capable of treating sinusitis, and having a medicinal property as a painkiller.

Accordingly, the inventors of the present invention have studied a substance capable of treating chronic obstructive pulmonary disease by controlling the expression of MUC5AC induced by TNF-$\alpha$ and inhibiting neutrophil infiltration, selected a compound among the compounds separated from *Magnoliae flos*, which is effective for inhibiting the expression of MUC5AC, and confirmed that an extract of *Magnoliae flos*, a fraction or an active fraction obtained by fractionation thereof with an organic solvent, or a compound separated therefrom may be used to treat chronic obstructive pulmonary disease by inhibiting inflammatory cells, inhibiting the production of reactive oxygen species, and reducing cytokines in the bronchoalveolar lavage fluid of a chronic obstructive pulmonary disease mouse model, thereby completing the present invention.

DISCLOSURE OF INVENTION

Technical Problem

An object of the present invention is to provide a pharmaceutical composition for preventing or treating chronic obstructive pulmonary disease, which comprises an extract of *Magnoliae flos*, or a fraction or an active fraction obtained by fractionation thereof with an organic solvent as an active ingredient.

Another object of the present invention is to provide a pharmaceutical composition for preventing or treating chronic obstructive pulmonary disease, which comprises a compound separated from a fraction of *Magnoliae flos* as an active ingredient.

Solution to Problem

In order to accomplish the above object, the present invention provides a pharmaceutical composition for preventing or treating chronic obstructive pulmonary disease, which comprises an extract of *Magnoliae flos* or a fraction or an active fraction obtained by fractionation thereof with an organic solvent as an active ingredient.

Further, the present invention provides a pharmaceutical composition for preventing or treating chronic obstructive pulmonary disease, which comprises a compound represented by the following Formula 1, a stereoisomer thereof, or a pharmaceutically acceptable salt thereof as an active ingredient:

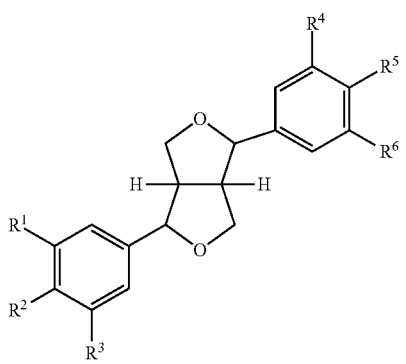

[Formula 1]

(In Formula 1 above, $R^1$, $R^4$, $R^5$, and $R^6$ are independently $C_{1-3}$ straight or branched chain alkyl, $C_{1-3}$ straight or branched chain alkoxy, or hydrogen; and
$R^2$ and $R^3$ are independently $C_{1-3}$ straight or branched chain alkyl, $C_{1-3}$ straight or branched chain alkoxy, or hydrogen, or $R^2$ and $R^3$ may together form

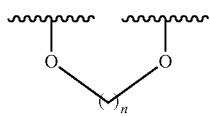

wherein n is an integer of 1 to 3).

In addition, the present invention provides a health functional food for preventing or ameliorating chronic obstructive pulmonary disease, which comprises an extract of *Magnoliae flos* or a fraction or an active fraction obtained by fractionation thereof with an organic solvent as an active ingredient.

In addition, the present invention provides a health functional food for preventing or ameliorating chronic obstructive pulmonary disease, which comprises a compound represented by Formula 1 above, a stereoisomer thereof, or a pharmaceutically acceptable salt thereof as an active ingredient.

In addition, the present invention provides a method for preventing or treating chronic obstructive pulmonary disease, which comprises administering a pharmaceutically effective amount of an extract of *Magnoliae flos* or a fraction or an active fraction obtained by fractionation thereof with an organic solvent to a subject suffering from chronic obstructive pulmonary disease.

In addition, the present invention provides the use of an extract of *Magnoliae flos*, a fraction or an active fraction obtained by fractionation thereof with an organic solvent as a pharmaceutical composition for preventing or treating chronic obstructive pulmonary disease.

Further, the present invention provides a method for preventing or treating chronic obstructive pulmonary disease, which comprises administering an effective amount of a compound represented by the following Formula 1, a stereoisomer thereof, or a pharmaceutically acceptable salt thereof to a subject suffering from chronic obstructive pulmonary disease:

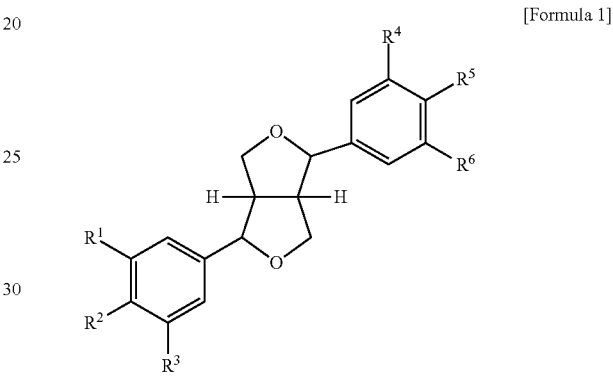

[Formula 1]

(In Formula 1 above, $R^1$, $R^4$, $R^5$, and $R^6$ are independently $C_{1-3}$ straight or branched chain alkyl, $C_{1-3}$ straight or branched chain alkoxy, or hydrogen; and
$R^2$ and $R^3$ are independently $C_{1-3}$ straight or branched chain alkyl, $C_{1-3}$ straight or branched chain alkoxy, or hydrogen, or $R^2$ and $R^3$ may together form

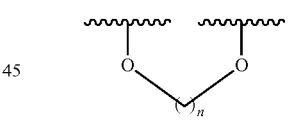

wherein n is an integer of 1 to 3).

In addition, the present invention provides the use of a compound represented by Formula 1 above, a stereoisomer thereof, or a pharmaceutically acceptable salt thereof as a pharmaceutical composition for preventing or treating chronic obstructive pulmonary disease.

Hereinafter, the present invention will be described in detail.

The present invention provides a pharmaceutical composition for preventing or treating chronic obstructive pulmonary disease, which comprises an extract of *Magnoliae flos* as an active ingredient.

The extract of *Magnoliae flos* may be prepared by a method comprising the following steps, but is not limited thereto:
(1) *Magnoliae flos* is dried to remove moisture and then pulverized;
(2) the *Magnoliae flos* dried in step (1) is extracted at room temperature by addition of an extraction solvent thereto; and (3) the extract obtained in step (2) is filtering and concentrated under a reduced pressure.

In the above method, any *Magnoliae flos*, either cultivated or commercially available, may be used without any limitation.

In step (1) of the above method, the drying may be any of drying under a reduced pressure, vacuum drying, boiling drying, spray drying, or lyophilization, but is not limited thereto.

In step (2) of the above method, the extraction may be carried out in a conventional way such as filtration, hot water extraction, immersion extraction, reflux cooling extraction, and ultrasonic extraction. The extraction may be carried out one to five times by hot water extraction, more specifically it may be repeated three times, but is not limited thereto. The extraction solvent may be added 0.1 to 10 times, preferably 0.3 to 5 times, to the dried *Magnoliae flos*. The extraction temperature may be 20 to 40° C., but is not limited thereto. In addition, the extraction time may be 12 to 48 hours, but is not limited thereto.

In step (2) of the above method, the extraction solvent may be water, a $C_1$ to $C_2$ lower alcohol, or a mixture thereof, but is not limited thereto.

In step (3) of the above method, the concentration under a reduced pressure may be conducted using a vacuum decompression concentrator or a vacuum rotary evaporator, but is not limited thereto.

The chronic obstructive pulmonary disease (COPD) refers to chronic bronchitis and emphysema, and usually refers to a phenomenon in which the airway narrows as chronic bronchitis and emphysema coexist in the lung.

In a specific embodiment of the present invention, the impact of an extract of *Magnoliae flos* on the expression of the MUC5AC protein was examined. As a result, the amount of MUC5AC secretion increased in a group of H292 cells treated with TNF-α. A comparison of the amount of MUC5AC secretion as a function of the amount of the *Magnoliae flos* extract with the group treated with TNF-α as a reference of 100% showed that the production of MUC5AC was inhibited in a manner depending on the concentration of the *Magnoliae flos* extract (see Table 4).

Therefore, the extract of *Magnoliae flos* of the present invention can be advantageously used for the prevention or treatment of chronic obstructive pulmonary disease (COPD).

The composition of the present invention may contain 0.1 to 99.9% by weight of the extract of *Magnoliae flos* of the present invention as an active ingredient based on the total weight of the composition, and it may comprise a pharmaceutically acceptable carrier, an excipient, or a diluent.

The composition of the present invention may be of various oral or parenteral formulations. Such formulations may be prepared with a diluent or an excipient such as a commonly used filler, an extender, a binder, a wetting agent, a disintegrant, a surfactant, and the like. Solid formulations for oral administration include tablets, pills, powders, granules, capsules, and the like, which may be prepared by blending at least one compound with at least one excipient such as starch, calcium carbonate, sucrose or lactose, gelatin, and the like. In addition to the simple excipient, a lubricant such as magnesium stearate, talc, and the like may also be used. Liquid formulations for oral administration include suspensions, solutions, emulsions, and syrups, which may be prepared with various excipients such as wetting agents, sweetening agents, fragrances, preservatives, and the like in addition to water and liquid paraffins as a simple diluent. Formulations for parenteral administration include sterile aqueous solutions, non-aqueous solutions, suspensions, emulsions, lyophilized formulations, and suppositories. Propylene glycol, polyethylene glycol, vegetable oils such as olive oil, injectable esters such as ethyl oleate, and the like may be used as the non-aqueous solvents and suspensions. Witepsol, macrogol, tween 61, cacao butter, laurin, glycerogelatin, and the like may be used as the suppository base.

The composition of the present invention may be administered orally or parenterally. For the parenteral administration, it is preferable to use an extracutaneous, intraperitoneal, rectal, intravenous, intramuscular, subcutaneous, intrauterine, or intracerebral injection. An extracutaneous use is the most preferable.

The dosage of the composition of the present invention varies with the patient's body weight, age, sex, health condition, diet, administration time, administration method, excretion rate, and severity of disease. The daily dosage is 0.01 to 1000 mg/kg, preferably 30 to 500 mg/kg, more preferably 50 to 300 mg/kg, based on the amount of the *Magnoliae flos* extract, and it may be administered 1 to 6 times a day.

The composition of the present invention may be used alone or in combination with surgery, radiation therapy, hormone therapy, chemotherapy, and the method of using biological response modifiers.

Further, the present invention provides a pharmaceutical composition for preventing and treating chronic obstructive pulmonary disease, which comprises a fraction or an active fraction obtained by fractionating an extract of *Magnoliae flos* with an organic solvent as an active ingredient.

The organic solvent may be selected from hexane, ethyl acetate, chloroform, butanol, and water, but is not limited thereto.

The fraction may be a hexane fraction, an ethyl acetate fraction, a chloroform fraction, or a water fraction obtained by sequentially fractionating the extract of *Magnoliae flos* with hexane, ethyl acetate, chloroform, and water in this order. According to a preferred embodiment of the present invention, the fraction may preferably be a hexane fraction, a chloroform fraction, or a water fraction obtained by sequentially fractionating the extract with hexane, chloroform, and water in this order.

The active fraction is Fraction 10 (Fr. 10) out of 10 additional fractions obtained by fractionating the chloroform fraction with a mixed solvent of hexane and ethyl acetate, in which hexane and ethyl acetate are mixed at a ratio of 3:1.

Further, the present invention provides a pharmaceutical composition for preventing or treating chronic obstructive pulmonary disease, which comprises a compound represented by the following Formula 1, a stereoisomer thereof, or a pharmaceutically acceptable salt thereof as an active ingredient:

[Formula 1]

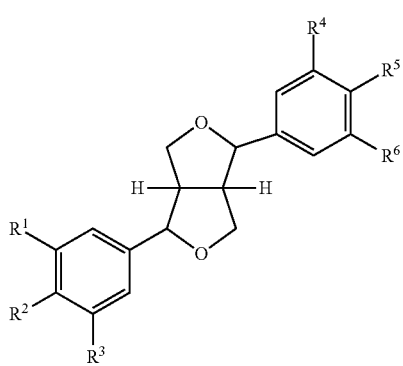

(In Formula 1 above, $R^1$, $R^4$, $R^5$, and $R^6$ are independently $C_{1-3}$ straight or branched chain alkyl, $C_{1-3}$ straight or branched chain alkoxy, or hydrogen; and $R^2$ and $R^3$ are independently $C_{1-3}$ straight or branched chain alkyl, $C_{1-3}$ straight or branched chain alkoxy, or hydrogen, or $R^2$ and $R^3$ may together form

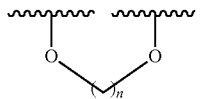

wherein n is an integer of 1 to 3).

The above compound is characterized by a compound represented by any one of the following Formulae 2 to 8:

[Formula 2]

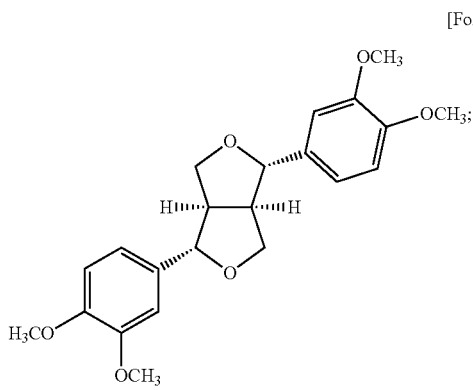

[Formula 3]

[Formula 4]

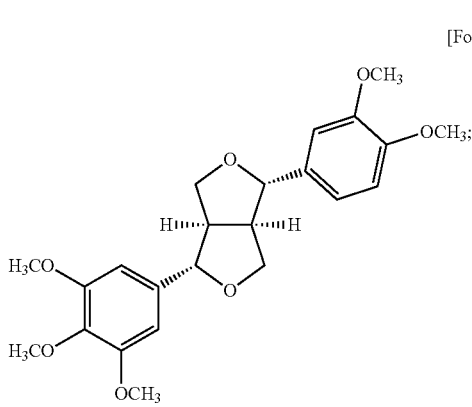

[Formula 5]

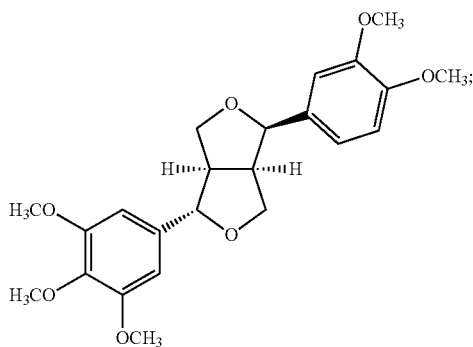

[Formula 6]

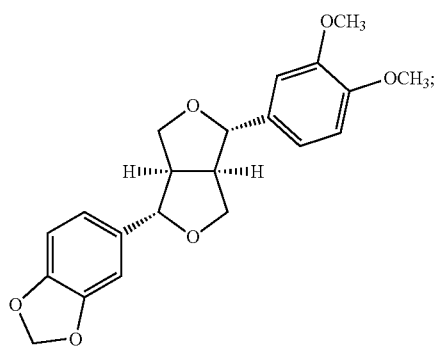

[Formula 7]

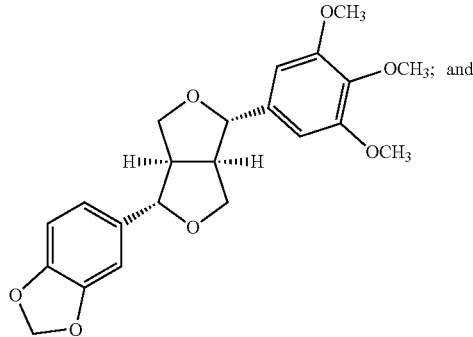

[Formula 8]

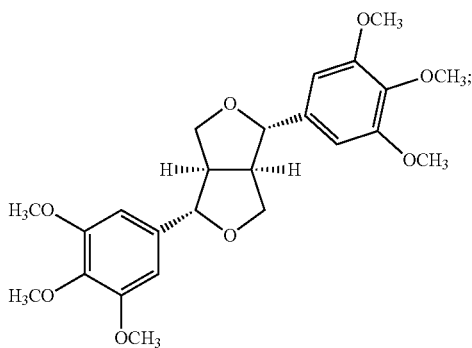

In a specific embodiment of the present invention, the impact of an extract of *Magnoliae flos* on the expression of the MUC5AC protein was examined. As a result, the amount of MUC5AC secretion increased in a group of H292 cells treated with TNF-α. A comparison of the amount of MUC5AC secretion as a function of the amount of the *Magnoliae flos* extract with the group treated with TNF-α as a reference of 100% showed that the production of MUC5AC was inhibited in a manner depending on the concentration of the *Magnoliae flos* extract (see Table 4). It was also confirmed that the compounds represented by Formulae 2, 3, 4, and 5 among the compounds represented by Formulae 2 to 8 above, separated from the fractions obtained from the extract of *Magnoliae flos*, inhibited the production of MUC5AC in a manner depending on concentration (see Table 6).

In addition, a COPD mouse model was prepared to confirm the effect of the active fraction (Fr. 10) of *Magnoliae flos* and the compounds separated therefrom on the treatment of chronic obstructive pulmonary disease, and the active fraction and the compounds separated therefrom were orally administered thereto. As a result, it was confirmed that the inhibition rates of inflammatory cell infiltration in the groups administered with the active fraction of *Magnoliae flos* and the compounds separated therefrom were similar to, or higher than, that of a drug control group treated with roflumilast (ROF) (see Table 8).

In addition, the inhibitory effect of the active fraction of *Magnoliae flos* and the compounds separated therefrom on the production of active oxygen species in the bronchoalveolar lavage fluid was examined. As a result, the groups administered with the active fraction of *Magnoliae flos* (30 mg/kg), Compound 2 (30 mg/kg), Compound 4 (30 mg/kg), Compound 6 (15 mg/kg, 30 mg/kg), Compound 7 (15 mg/kg, 30 mg/kg), and Compound 8 (15 mg/kg, 30 mg/kg) showed higher rates of inhibiting reactive oxygen than that of the drug control group treated with ROF (roflumilast) (see Table 8).

In addition, extensive infiltration of inflammatory cells was observed around the bronchial and alveolar compartments in the COPD-induced group as compared with the normal group, whereas the infiltration of inflammatory cells was reduced in the roflumilast treated group. The infiltration of inflammatory cells was also reduced in the groups administered with the active fraction and the compounds of *Magnoliae flos* as compared with the COPD-induced group. In particular, the reduction in the infiltration of inflammatory cells was remarkably observed in the 30 mg/kg administration group among the groups administered with the active fraction of *Magnoliae flos* (see FIG. 5).

Further, the reduction in the cytokine levels in the bronchoalveolar lavage fluid was examined, which showed that the groups administered with the active fraction of *Magnoliae flos* and most of the compounds thereof showed inhibition rates similar to, or higher than, that of the drug control group treated with ROF (see Table 10).

Therefore, the fractions or the active fraction of *Magnoliae flos*, or the compounds separated therefrom of the present invention can be used as an active ingredient of a pharmaceutical composition for the prevention and treatment of chronic obstructive pulmonary disease.

The compound represented by Formula 1 of the present invention may be used in the form of a pharmaceutically acceptable salt. An acid addition salt formed by a pharmaceutically acceptable free acid is desirable as the salt. The acid addition salt is formed from an inorganic acid such as hydrochloric acid, nitric acid, phosphoric acid, sulfuric acid, hydrobromic acid, hydroiodic acid, nitrous acid, and phosphorous acid; and a non-toxic organic acid such as aliphatic mono- and dicarboxylates, phenyl-substituted alkanoates, hydroxyalkanoates and alkanedioates, aromatic acids, aliphatic and aromatic sulfonic acids; and an organic acid such as acetic acid, benzoic acid, citric acid, lactic acid, maleic acid, gluconic acid, methanesulfonic acid, 4-toluenesulfonic acid, tartaric acid, and fumaric acid. Such pharmaceutically non-toxic salts include sulfate, pyrosulfate, bisulfate, sulfite, bisulfite, nitrate, phosphate, monohydrogen phosphate, dihydrogen phosphate, metaphosphate, pyrophosphate chloride, bromide, iodide, fluoride, acetate, propionate, decanoate, caprylate, acrylate, formate, isobutyrate, caprate, heptanoate, propiolate, oxalate, malonate, succinate, suverate, sebacate, fumarate, malate, butyne-1,4-dioate, hexane-1,6-dioate, benzoate, chlorobenzoate, methyl benzoate, dinitrobenzoate, hydroxybenzoate, methoxybenzoate, phthalate, terephthalate, benzene sulfonate, toluene sulfonate, chlorobenzene sulfonate, xylene sulfonate, phenyl acetate, phenyl propionate, phenyl butyrate, citrate, lactate, β-hydroxybutyrate, glycolate, maleate, tartrate, methanesulfonate, propanesulfonate, naphthalene-1-sulfonate, naphthalene-2-sulfonate, and mandelate.

The acid addition salt according to the present invention may be prepared by a conventional method, for example, by dissolving the compound represented by Formula 1 in an organic solvent such as methanol, ethanol, acetone, methylene chloride, acetonitrile, and the like, followed by filtration and drying of a precipitate formed by addition of an organic or inorganic acid, or by distillation of the solvent and excessive acid under a reduced pressure, followed by drying or crystallization in an organic acid.

In addition, a base can be used to prepare a pharmaceutically acceptable metal salt. An alkali metal or alkaline earth metal salt is obtained, for example, by dissolving the compound in an excessive amount of an alkali metal hydroxide or alkaline earth metal hydroxide solution, filtering the insoluble compound salt, and evaporating and drying the filtrate. Here, a sodium, potassium, or calcium salt is preferable as the metal salt. Also, the corresponding silver salt is obtained by reacting an alkali metal or alkaline earth metal salt with a suitable silver salt (e.g., silver nitrate).

Furthermore, the present invention covers not only the compound represented by Formula 1 or pharmaceutically acceptable salts thereof, but also any solvates, hydrates, isomers, and the like, which can be prepared therefrom.

Further, the present invention provides a health functional food for preventing or ameliorating chronic obstructive pulmonary disease, which comprises an extract of *Magnoliae flos*, or a fraction or an active fraction obtained by fractionation thereof with an organic solvent as an active ingredient.

In addition, the present invention provides a health functional food for preventing or ameliorating chronic obstructive pulmonary disease, which comprises a compound represented by the following Formula 1, a stereoisomer thereof, or a pharmaceutically acceptable salt thereof as an active ingredient:

[Formula 1]

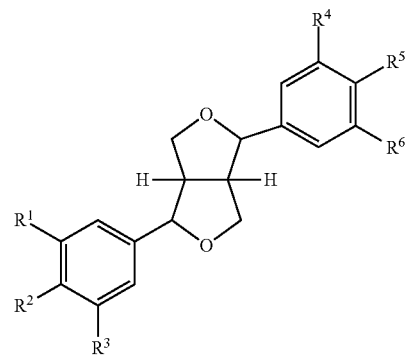

(In Formula 1 above, $R^1$, $R^4$, $R^5$, and $R^6$ are independently $C_{1-3}$ straight or branched chain alkyl, $C_{1-3}$ straight or branched chain alkoxy, or hydrogen; and $R^2$ and $R^3$ are independently $C_{1-3}$ straight or branched chain alkyl, $C_{1-3}$ straight or branched chain alkoxy, or hydrogen, or $R^2$ and $R^3$ may together form

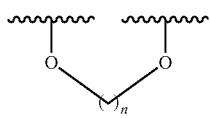

wherein n is an integer of 1 to 3).

The above compound is characterized by a compound represented by any one of the following Formulae 2 to 8:

[Formula 2]

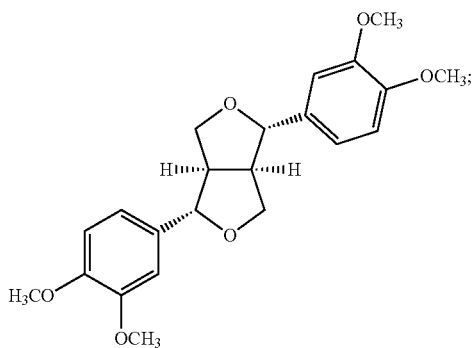

[Formula 3]

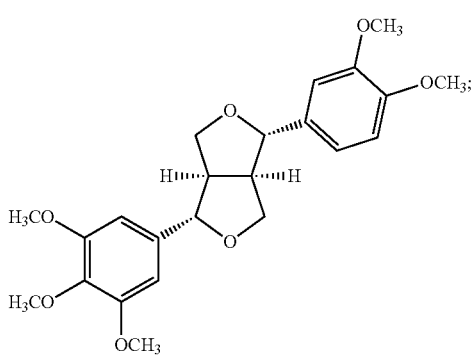

[Formula 4]

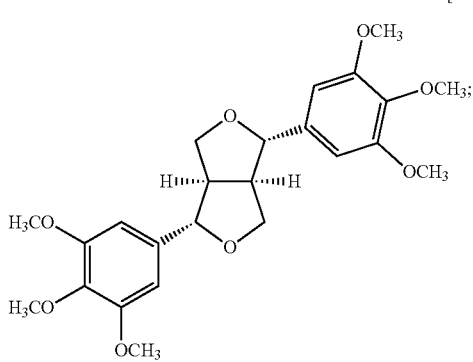

[Formula 5]

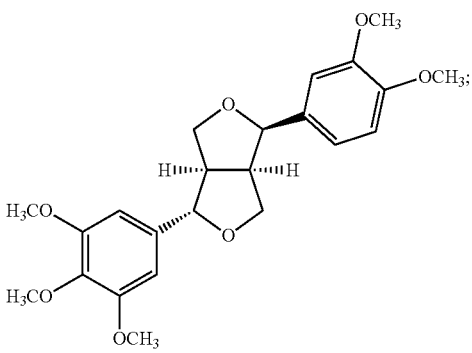

[Formula 6]

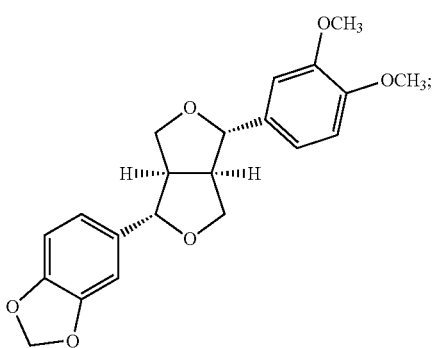

[Formula 7]

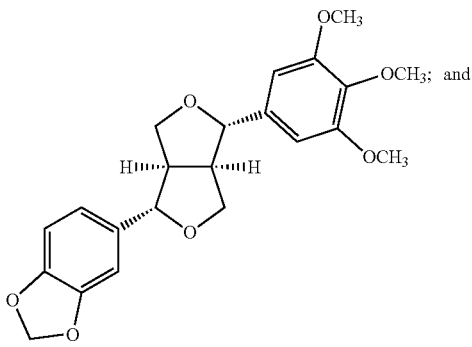

and

[Formula 8]

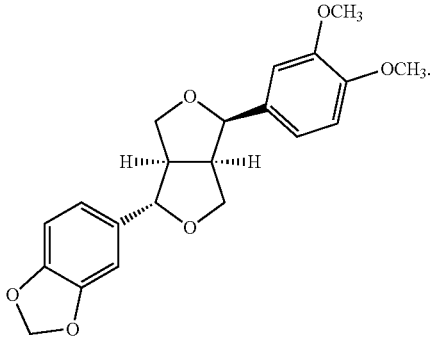

The health functional food of the present invention may contain various flavors or natural carbohydrates as an additional ingredient. The above-mentioned natural carbohydrates are monosaccharides such as glucose and fructose, disaccharides such as maltose and sucrose, polysaccharides such as dextrin and cyclodextrin, and sugar alcohols such as xylitol, sorbitol, and erythritol. Natural sweeteners such as thaumatin and stevia extracts and synthetic sweeteners such as saccharin and aspartame may be used as a sweetener. The content of the natural carbohydrate may be in the range of 0.01 to 0.04 part by weight, particularly about 0.02 to 0.03 part by weight, per 100 parts by weight of the health functional food of the present invention.

In addition to the above, the health functional food of the present invention may contain various nutrients, vitamins, electrolytes, savors, colorants, pectic acid and salts thereof, alginic acid and its salts, protective colloid thickeners, pH adjusters, stabilizers, preservatives, glycerin, alcohols, carbonating agents used in carbonated drinks, and the to like. These components may be used alone or in combination thereof. The content of such additives is not critical, but is generally in the range of 0.01 to 0.1 part by weight per 100 parts by weight of the health functional food of the present invention.

Further, the present invention provides a method for preventing or treating chronic obstructive pulmonary disease, which comprises administering an extract of *Magnoliae flos* or a fraction or an active fraction obtained by fractionation thereof with an organic solvent to a subject suffering from chronic obstructive pulmonary disease.

In addition, the present invention provides the use of an extract of *Magnoliae flos* or a fraction or an active fraction obtained by fractionation thereof with an organic solvent as a pharmaceutical composition for preventing or treating chronic obstructive pulmonary disease.

In addition, the present invention provides a method for preventing or treating chronic obstructive pulmonary disease, which comprises administering an effective amount of a compound represented by the following Formula 1, a stereoisomer thereof, or a pharmaceutically acceptable salt thereof to a subject suffering from chronic obstructive pulmonary disease:

[Formula 1]

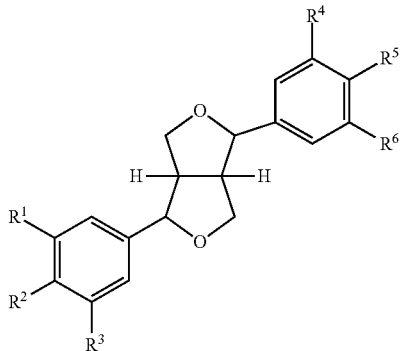

(In Formula 1 above, $R^1$, $R^4$, $R^5$, and $R^6$ are independently $C_{1-3}$ straight or branched chain alkyl, $C_{1-3}$ straight or branched chain alkoxy, or hydrogen; and
$R^2$ and $R^3$ are independently $C_{1-3}$ straight or branched chain alkyl, $C_{1-3}$ straight or branched chain alkoxy, or hydrogen, or $R^2$ and $R^3$ may together form

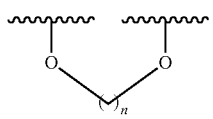

wherein n is an integer of 1 to 3).

In addition, the present invention provides the use of a compound represented by Formula 1 above, a stereoisomer thereof, or a pharmaceutically acceptable salt thereof as a pharmaceutical composition for preventing or treating chronic obstructive pulmonary disease.

Advantageous Effects of Invention

The extract of *Magnoliae flos*, the fraction or the active fraction obtained by fractionation thereof with an organic solvent, or the compound separated therefrom according to the present invention inhibits the expression of MUC5AC induced by TNF-α and its promoter activity in human lung cancer mucosal cells (H292), reduces the number of inflammatory cells in the bronchoalveolar lavage fluid of the chronic obstructive pulmonary disease mouse model, inhibits the production of reactive oxygen species, and reduces cytokines. Therefore, it can be advantageously used for the treatment of chronic obstructive pulmonary disease by way of inhibiting the expression of MUC5AC and the infiltration of neutrophils.

BRIEF DESCRIPTION OF THE DRAWINGS

FIG. 1 is a diagram illustrating a process of preparing an extract of *Magnoliae flos* and a fraction and an active fraction thereof.

FIG. 2 shows the results of thin film chromatography to prepare an active fraction from an extract of *Magnoliae flos*.

FIG. 3a, FIG. 3b, and FIG. 3c show the results of ultraperformance liquid chromatography to separate and purify the active fraction of *Magnoliae flos*.

FIG. 4a and FIG. 4b show the results of mass spectrometry of the compounds separated from the extract of *Magnoliae flos and their chemical formulae*.

FIG. 5a, FIG. 5b, and FIG. 5c show the results of pathological examination of pulmonary tissue in a COPD model treated with the active fraction and the compounds of *Magnoliae flos*.

BEST MODE FOR CARRYING OUT THE INVENTION

Hereinafter, the present invention will be described in more detail with reference to the following examples and test examples.

However, these examples and test examples are set forth to illustrate the present invention in detail, and the scope of the present invention is not limited thereto.

<EXAMPLE 1> PREPARATION OF AN EXTRACT OF *MAGNOLIAE FLOS*

*Magnoliae flos* (80 kg) was dried in the shade with a drier (at 50-55° C.) to remove moisture and then pulverized to a size of about 1 cm. Methanol (600 liters) was added per the dry weight of the pulverized powder sample, followed by extraction at room temperature. Then, upon filtration and concentration under a reduced pressure, a methanol extract of *Magnoliae flos* (12 kg; extraction yield of 14.5%) was obtained.

<EXAMPLE 2> PREPARATION OF FRACTIONS OF *MAGNOLIAE FLOS*

Fractions of *Magnoliae flos* were prepared from the methanol extract of *Magnoliae flos* obtained in <Example 1> above, as follows.

Specifically, the methanol extract of *Magnoliae flos* (500 g) was suspended in 2.5 liters of distilled water, and the same amount of hexane was added thereto for separation into a hexane layer and a water layer, which were filtered and concentrated under a reduced pressure to obtain a hexane fraction (87.0 g). Then, the remaining water layer from which the hexane fraction had been removed was added with the same amount of chloroform in the same manner as above, to thereby obtain a chloroform fraction (57.6 g). The remaining water layer was concentrated to obtain 310 g of a water fraction (see FIG. 1).

<EXAMPLE 3> PREPARATION OF ADDITIONAL FRACTIONS

Flash column chromatography was performed to separate and prepare additional fractions from the fraction of *Magnoliae flos* obtained in <Example 2> above.

Specifically, an open column (10 cm×50 cm; resin; silica gel, 800 g) was mounted, and the chloroform layer among the fractions obtained in <Example 2> above was loaded. Hexane/ethyl acetate was used as a solvent, and thin film chromatography (Merck, normal phase and reverse phase plate) was carried out under a normal phase (a developing solvent of hexane:ethyl acetate=3:1) to obtain 10 additional fractions (Frs. 1-10) (see Table 1, FIGS. 1 and 2).

TABLE 1

|  | Fraction | Solvent (hexane/ethyl acetate, L) | Number (bottle number) | Weight (g) |
| --- | --- | --- | --- | --- |
| Fr. 1 | Fraction 1 | 15:1, 3 L | 13 | 0.34 |
| Fr. 2 | Fraction 2 |  | 14 | 0.96 |
| Fr. 3 | Fraction 3 |  | 15 | 1.64 |
| Fr. 4 | Fraction 4 | 10:1, 3 L | 16 | 1.64 |
| Fr. 5 | Fraction 5 |  | 17-20 | 2.38 |
| Fr. 6 | Fraction 6 | 8:1, 5 L | 21-22 | 9.45 |
| Fr. 7 | Fraction 7 | 6:1, 6 L | 23-25 | 2.38 |
| Fr. 8 | Fraction 8 | 4:1, 2 L | 26-27 | 3.27 |
| Fr. 9 | Fraction 9 |  | 28-29 | 0.56 |
| Fr. 10 | Fraction 10 | 1:1, 6 L | 30-46 | 49.28 |

<EXAMPLE 4> ANALYSIS OF THE EXTRACT AND THE FRACTIONS OF *MAGNOLIAE FLOS*

Ultraperformance liquid chromatography (UPLC) was carried out to analyze the extract and the fractions obtained in <Example 1> and <Example 3>.

Specifically, the extract and the fractions of *Magnoliae flos* were filtered once with a 0.25 mm membrane filter for UPLC. Then, a column (Waters BEH C18 column, 2.1×100 mm, 1.7 μm) was mounted on to a UPLC instrument (Waters UPLC-QTOF-MS), and each fraction thus filtered in the amount of 5 μl was loaded. At this time, acetonitrile+0.1% formic acid/water+0.1% formic acid (10:90→100:0 (v/v)) was used as a solvent, and the elution rate was 0.4 ml/min. UV and MS (mass spectrometry) were used as detectors to confirm the degree of separation of the substances separated by the UPLC in a chromatographic type (see FIGS. 3*a*, 3*b*, and 3*c*).

<EXAMPLE 5> SEPARATION OF SMALL FRACTIONS FROM FRACTION 10 (FR. 10)

Small fractions were prepared from Fraction 10 among the 10 additional fractions obtained in <Example 3> above, as follows.

Specifically, an open column (18 cm×75 cm; resin; ODS, 3,000 g) was mounted, and Fraction 10 was loaded repeatedly. Methanol/water (40% methanol (5 L)→50% methanol (2 L)→70% methanol (2 L)→100% methanol (2 L)) was used as a solvent. For each solvent, Fraction 10 was subjected to ultraperformance liquid chromatography (Thermo FINNIGAN SURVEYOR, USA) mounted with a column (YMC PAK Pro C8, 5 mm, 4.6×250 mm) at an elution rate of 1 ml/min and detected at a wavelength of 254 nm, to thereby obtain four small fractions (FIGS. 10A-D).

<EXAMPLE 6> SEPARATION OF COMPOUNDS FROM THE SMALL FRACTIONS (FIGS. 10A-D)

Compounds were separated from the small fractions obtained in <Example 5> above, as follows.

Specifically, Small Fraction 10A was fractionated with an open column (2 cm×25 cm; resin; silica gel (YMC-Pack ODS-AQ-HG, 10 μm)) under an isocratic condition of 55% methanol to obtain Compound 1 (dimethylpinoresinol, 2.1 g) represented by Formula 2 and Compound 4 (epimagnolin, 1.5 g) represented by Formula 5, which have a lignan structure and the following physical properties; fractionated with an open column (10 cm×90 cm; resin; silica gel (YMC GEL SIL-HG 20 mm, 20 μm), 220 g) under an isocratic condition of hexane/chloroform/ethyl acetate (5:2:1) to obtain Compound 2 (magnolin, 6.3 g) represented by Formula 3, which has a lignan structure and the following physical properties; and fractionated with an open column (10 cm×90 cm; resin; silica gel (silia-p Flash silica gel, 40-63 μm), 1,700 g) under an isocratic condition of chloroform/acetone/methanol (40:1:0.1) to obtain Compound 3 (dimethylliroresinol, 1.71 g) represented by Formula 4, which has a lignan structure and the following physical properties.

Small Fraction 10C was fractionated with a column (3 cm×50 cm; resin; silica gel (YMC pack silica gel, 25 μm), 120 g) under an isocratic condition of chloroform/ethyl acetate (19:1) to obtain Compound 5 (dimethoxyaschantin, 6.96 g) represented by Formula 6, Compound 6 (aschantin, 3.39 g) represented by Formula 7, and Compound 7 (fargesin, 3.86 g) represented by Formula 8, which have a lignan structure and the following physical properties (see Table 2 and FIGS. 4*a* and 4*b*).

TABLE 2

| Type | Data |
| --- | --- |
| Formula 2 (S1) (dimethylpinoresinol) | Amorphous solid; [α]D +55.0 (CHCl3, c 2.4); HRESIMS m/z 387.1809 [M + H]+. 1H-NMR (500 MHz, CDCl3) δ 3.12 (2H, m, H-1/H-5), 3.87 (6H, s, 3', 3"-OMe), 3.88 (2H, m, H-4a/H-8a), 3.90 (6H, s, 4', 4"-OMe), 4.26 (2H, m, H-4b/H-8b), 4.76 (2H, d, J = 4.3 Hz, H-2/H-6), 6.85 (2H, d, J = 8.0 Hz, H-5'/H-5"), 6.89 (2H, dd, J = 2.0, 8.5 Hz, H-6'/H-6"), 6.91 (2H, d, J = 2.0 Hz, H-2'/H-2"); 13C-NMR (125 MHz, CDCl3) δ 54.2 (C-1/C-5), 55.9 (OMe, C-3'/C-4'/C-3"/C-4"), 71.7 (C-4/C-8), 85.8 (C-2/C-6), 109.3 (C-2'/C-2"), 111.1 (C-5'/C-5"), 118.3 (C-6'/C-6"), 133.6 (C-1'/C-1"), 148.6 (C-4'/C-4"), 149.2 (C-3'/C-3"). |

TABLE 2-continued

| Type | Data |
|---|---|
| Formula 3(S2) (magnolin) | Viscous oil; [α]D +44.0 (CHCl3, c 2.0); HRESIMS m/z 417.1884 [M + H]+. 1H-NMR (500 MHz, CDCl3) δ 3.11 (2H, m, H-1/H-5), 3.83 (6H, d, J = 1.5 Hz, OMe), 3.87 (6H, d, J = 1.0 Hz, OMe), 3.90 (3H, d, J = 1.5 Hz, OMe), 3.92 (2H, dd, J = 3.5, 9.0 Hz, H-4a/H-8a), 4.28 (2H, m, H-4b/H-8b), 4.76 (2H, dd, J = 4.0, 10.5 Hz, H-2/H-6), 6.57 (2H, s, H-2'/H-6'), 6.85-6.91 (3H, m, Aromatic H, H-5''/H-6''/H-2''); 13C-NMR (125 MHz, CDCl3) δ 54.1 (C-5), 54.4 (C-1), 55.9 (OMe, C-3''), 56.0 (OMe, C-4''), 56.2 (OMe, C-3'/C-5'), 60.9 (OMe, C-4'), 71.8 (C-8), 72.0 (C-4), 85.7 (C-6), 86.0 (C-2), 102.8 (C-2'/C-6'), 109.2 (C-2''), 111.1 (C-5''), 118.2 (C-6''), 133.5 (C-1''), 136.8 (C-1'), 137.5 (C-4'), 148.7 (C-4''), 149.2 (C-3''), 153.4 (C-3'/C-5'). |
| Formula 4 (S3) (dimethylliroresinol) | Amorphous solid; [α]D +42.9 (CHCl3, c 1.0); HRESIMS m/z 447.2069 [M + H]+. 1H-NMR (500 MHz, CDCl3) δ 3.10 (2H, m, H-1/H-5), 3.83 (6H, s, 4', 4''-OMe), 3.87 (12H, s, 3', 3'', 5', 5''-OMe), 3.94 (2H, dd, J = 3.6, 9.2 Hz, H-4a/H-8a), 4.32 (2H, m, H-4b/H-8b), 4.75 (2H, d, J = 4.3 Hz, H-2/H-6), 6.57 (4H, s, ArH); 13C-NMR (125 MHz, CDCl3) δ 54.4 (C-1/C-5), 56.3 (3', 3'', 5', 5''-OMe), 60.9 (4', 4''-OMe), 72.0 (C-4/C-8), 86.0 (C-2/C-6), 103.0 (C-2'/C-2''/C-6'/C-6''), 136.8 (C-1'/C-1''), 137.7 (C-4'/C-4''), 153.5 (C-3'/C-3''/C-5'/C-5''). |
| Formula 5 (S4) (epimagnolin) | Colorless oil; [α]D +107.3 (CHCl3, c 0.50); HRESIMS m/z 417.1914 [M + H]+. 1H-NMR (500 MHz, CD3OD) δ 2.95 (1H, m, H-5), 3.29 (1H, m, H-8b), 3.41 (1H, m, H-1), 3.78-3.88 (2H, m, overlapped with OMe, H-8a/H-4a), 3.82-3.84 (12H, s, 3', 4', 5', 3'', 4''-OMe), 4.14 (1H, d, J = 9.6 Hz, H-4b), 4.47 (1H, d, J = 6.9 Hz, H-6), 4.89 (1H, d, J = 5.6 Hz, H-2), 6.94 (4H, d, J = 5.2 Hz, H-5'/H-6'/H-5''/H-6''), 6.98 (1H, s, H-2''), 7.00 (1H, s, H-2'); 13C-NMR (125 MHz, CD3OD) δ 49.7 (C-1), 54.2 (C-5), 55.0 (3', 4', 5', 3'', 4''-OMe), 69.1 (C-8), 70.5 (C-4), 81.8 (C-2), 87.7 (C-6), 109.5 (C-2'), 109.7 (C-2''), 111.5 (C-5', C-5''), 117.8 (C-6'), 118.4 (C-6''), 131.3 (C-1'), 133.9 (C-1''), 148.1 (C-4'), 148.8 (C-4''), 148.9 (C-3'), 149.2 (C-3''). |
| Formula 6 (S5) (dimethoxy aschantin) | Colorless oil; [α]D +59.5 (CHCl3, c 2.13); HRESIMS m/z 371.1501 [M + H]+. 1H-NMR (500 MHz, CDCl3) δ 3.08 (2H, m, H-1/H-5), 3.88 (3H, s, 4'-OMe), 3.86-3.89 (2H, m, overlapped with OMe, H-4a/H-8a), 3.90 (3H, s, 3'-OMe), 4.25 (2H, m, H-4b/H-8b), 4.74 (2H, t, J = 5.5 Hz, H-2/H-6), 5.95 (2H, s, —OCH2O—), 6.77-6.91 (6H, m, ArH, H-2'/H-2''/H-5'/H-5''/H-6'/H-6''); 13C-NMR (125 MHz, CDCl3) δ 54.2 (C-1), 54.3 (C-5), 55.9 (4'-OMe), 56.0 (3'-OMe), 71.7 (C-8), 71.8 (C-4), 85.76, 85.82 (C-2/C-6) 101.1 (—OCH2O—), 106.5 (C-2''), 108.2 (C-5''), 109.2 (C-2'), 111.1 (C-5'), 118.3 (C-6'), 119.4 (C-6''), 133.5 (C-1'), 135.1 (C-1''), 147.1 (C-4''), 148.0 (C-3''), 148.6 (C-4'), 149.2 (C-3'). |
| Formula 7 (S6) (aschantin) | Viscous oil; [α]D +49.0 (CHCl3, c 1.33); HRESIMS m/z 401.1570 [M + H]+. 1H-NMR (500 MHz, CDCl3) δ 3.08 (2H, m, H-1/H-5), 3.84 (3H, s, 4'-OMe), 3.88 (6H, s, 3', 5'-OMe), 3.89 (1H, dd, J = 4.0, 9.0 Hz, H-4a), 3.91 (1H, dd, J = 4.0, 9.0 Hz, H-8a), 4.26 (1H, dd, J = 6.5, 9.0 Hz, H-4b), 4.29 (1H, dd, J = 6.5, 9.0 Hz, H-8b), 4.73 (2H, t, J = 4.4 Hz, H-2/H-6), 5.95 (2H, s, —OCH2O—), 6.57 (2H, s, H-2'/H-6'), 6.79 (1H, d, J = 8.0 Hz, H-5''), 6.80 (1H, dd, J = 1.5, 8.0 Hz, H-6''), 6.85 (1H, d, J = 1.5 Hz, H-2''); 13C-NMR (125 MHz, CDCl3) δ 54.3 (C-5), 54.4 (C-1), 56.2 (3', 5'-OMe), 60.9 (4'-OMe), 71.7 (C-4), 72.0 (C-8), 85.8 (C-6), 86.0 (C-2), 101.1 (—OCH2O—), 102.8 (C-2'/C-6'), 106.5 (C-2''), 108.2 (C-5''), 119.4 (C-6''), 135.0 (C-1''), 136.8 (C-1'), 137.5 (C-4'), 147.1 (C-4''), 148.0 (C-3''), 153.4 (C-3'/C-5'). |
| Formula 8 (S7) (fargesin) | Amorphous solid; [α]D +93.5 (CHCl3, c 0.6); HRESIMS m/z 371.1467 [M + H]+. 1H-NMR (500 MHz, CDCl3) δ 2.88 (1H, m, H-5), 3.28-3.35 (2H, m, H-8a/H-1), 3.82-3.86 (2H, m, H-8b/H-4a), 3,88 (3H, s, OMe), 3.90 (3H, s, OMe), 4.13 (1H, dd, J = 0.7, 9.4 Hz, H-4b), 4.43 (1H, d, J = 7.0 Hz, H-6), 4.87 (1H, d, J = 5.0 Hz, H-2), 5.95 (2H, dd, J = 1.5, 2.3 Hz, —OCH2O—, H-3''/H-4''), 6.76-6.87 (5H, m ArH), 6.93 (1H, s, ArH); 13C-NMR (125 MHz, CDCl3) δ 50.2 (C-1), 54.6 (C-5), 55.91 (OMe, C-3'), 55.94 (OMe, C-4'), 69.8 (C-8), 71.0 (C-4), 82.0 (C-2), 87.7 (C-6), 101.0 (—OCH2O—, C-3''/C-4''), 106.5 (C-2''), 108.2 (C-2'), 109.0 (C-5'), 111.1 (C-5''), 117.7 (C-6''), 119.6 (C-6'), 130.9 (C-1''), 135.2 (C-1'), 147.2 (C-3''), 148.0 (C-4''), 148.3 (C-3'), 148.9 (C-4'). |

<TEST EXAMPLE 1> CYTOTOXICITY OF THE EXTRACT AND THE FRACTIONS OF *MAGNOLIAE FLOS* IN HUMAN LUNG CANCER MUCOSA CELLS (H292)

Prior to the main tests, in order to confirm the cytotoxicity of the extract and the fractions of *Magnoliae flos* to H292 cells, a test according to the method described in the literature (Ishiyama et al., Talanta, 44, pp. 1299-1305, 1997; Tominaga et al., Anal. Commun., 36, pp. 47-50, 1999) was carried out.

<1-1> Preparation and Culturing of Cells

H292 (CRL-1848, American Type Culture Collection) cells were cultured in an RPMI medium supplemented with 10% fetal bovine serum and antibiotics (SH30027.01, RPMI 1640, Gibco) and cultured in humidified 5% $CO_2$ at 37° C. TNF-α (300-01A, Peprptech, USA) was purchased for use.

<1-2> Cell Viability Assay

The above cells were cultured in a 96-well plate at $1\times10^3$ cells/well for 24 hours and further cultured for 1 or 2 days together with the extract or the fractions of *Magnoliae flos*. The cell viability was read in triplicate using a reading kit (Cell Counting Kit-8, CK04-01, Dojindo Molecular Technologies, ML) according to the manufacturer's manual. Absorbance was measured using a reader (VERSAmax microplate reader, SMP500-14915, Molecular Devices, USA), and the measured absorbance was converted to the cell number using a standard curve.

Specifically, H292 cells were suspended in an RPMI medium (Gibco) supplemented with 10% fetal bovine serum at a concentration of $5\times10^4$ cells/nal, and 100 µl thereof each was inoculated on a 96-well plate and allowed to attach for 12 hours, which were treated with the extracts in different concentrations and then cultured for 24 hours. Thereafter, as described in the CCK-8 (Dojindo) kit, which can count the number of cells, the CCK-8 solution (10 µl) was mixed with 90 µl of the medium, and 100 µl thereof was added per well. After incubation for a minimum of 30 minutes to a maximum of 4 hours, the absorbance was measured at 570 nm. The cell viability was calculated according to the following Equation 1 with a negative control group treated with 0.2% DMSO as a reference of 100%, and the results are shown in the following Table 3.

Cell viability=(Extract treated OD 570 nm value)× 100/(Negative control group OD 570 nm value)   [Equation 1]

As a result of the test in which the cell viability of H292 cells with respect to the concentrations of the extract and the fractions was examined, it was confirmed that there was no cytotoxicity at 40 µg/mL or less as shown in Table 3.

TABLE 3

| Sample | Concentration (µg/mL) | Viability of H292 cells (%, average ± deviation) |
|---|---|---|
| Negative control group | 0 | 100.00 ± 1.91 |
| *Magnoliae flos* extract | 10 | 101.27 ± 5.11 |
| | 20 | 101.10 ± 4.24 |
| | 40 | 97.46 ± 2.42 |
| Hex | 10 | 99.62 ± 2.56 |
| | 20 | 98.47 ± 0.74 |
| | 40 | 93.77 ± 1.70 |
| $CHCl_3$ | 10 | 102.97 ± 1.53 |
| | 20 | 108.36 ± 2.28 |
| | 40 | 113.69 ± 3.88 |
| BuOH | 10 | 103.70 ± 4.04 |
| | 20 | 102.04 ± 2.54 |
| | 40 | 101.91 ± 2.77 |

TABLE 3-continued

| Sample | Concentration (µg/mL) | Viability of H292 cells (%, average ± deviation) |
|---|---|---|
| D.W. | 10 | 104.74 ± 2.78 |
| | 20 | 111.60 ± 3.89 |
| | 40 | 117.66 ± 4.81 |

<TEST EXAMPLE 2> EFFECT OF THE EXTRACT AND THE FRACTIONS OF *MAGNOLIAE FLOS* ON THE EXPRESSION OF THE MUC5AC PROTEIN

A test according to the method described in the literature (Sikder, M A. et al., Phytotherapy research: PTR. 28, 62-8. 2014) was carried out to see whether the extract and the fractions of *Magnoliae flos* inhibit the expression of the MUC5AC protein induced by TNF-α in H292 cells.

Specifically, MUC5AC immunoassay induced by TNF-α was used. For the preparation of cells, H292 cells were dispensed on to a 48-well plate at a concentration of $2\times10^4$ cells/well, allowed to attach for 24 hours, and then cultured for 24 hours in a medium containing 0.1% FBS, which were treated with 20 µg/mL or 40 µg/mL of the extract for 2 hours, treated with TNF-α at a concentration of 20 ng/mL, and cultured for 12 hours. Thereafter, the cells were recovered and centrifuged, and the supernatant (50 µL) was then dispensed on to a 96-well plate and dried in a thermostat set at 50° C. They were washed with PBS supplemented with 1% BSA and reacted with an MUC5AC antibody (ab3649, abcam) at room temperature for 2 hours. A secondary antibody was dispensed thereto for reaction for 2 hours. They were washed again with PBS and then reacted with a 3,3',5,5'-tetramethylbenzidine peroxide solution (54827-17-7, Sigma-Aldrich) for 20 minutes. After the reaction was stopped with a sulfuric acid solution, the degree of color development at 450 nm was measured with a microplate reader (VERSAmax microplate reader, SMP500-14915, Molecular Devices, USA) (8. Sikder, M. A., Lee, H. J., Mia, M. Z., Park, S. H., Ryu, J., Kim, J. H., Min, S. Y., Hong, J. H., Seok, J. H. & Lee, C. J. (2014) Inhibition of TNF-α-induced MUC5AC mucin gene expression and production by wogonin through the inactivation of NF-kappaB signaling in airway epithelial cells, Phytotherapy research: PTR. 28, 62-8; Takeyama, K., Dabbagh, K., Lee, H. M., Agusti, C., Lausier, J. A., Ueki, I. F., Grattan, K. M. & Nadel, J. A. (1999) Epidermal growth factor system regulates mucin production in airways, Proceedings of the National Academy of Sciences of the United States of America. 96, 3081-6).

As a result, as shown in Table 4, the amount of MUC5AC secretion increased in the group treated with TNF-α. When the amounts of MUC5AC secretion as treated with the extract and the fractions were compared with the group treated with TNF-α as a reference of 100%, it was confirmed that the production of MUC5AC was inhibited in a manner depending on the concentrations of the extract and the fractions of *Magnoliae flos*.

TABLE 4

| Sample | Concentration (µg/mL) | TNF-α (20 ng/mL) | MUC5AC secretion (Relative amount to TNF-α treated group, %) | Inhibition rate (%) |
|---|---|---|---|---|
| Negative control group | 0 | – | 68.12 ± 0.86 | 100 |

TABLE 4-continued

| Sample | Concentration (μg/mL) | TNF-α (20 ng/mL) | MUC5AC secretion (Relative amount to TNF-α treated group, %) | Inhibition rate (%) |
|---|---|---|---|---|
| TNF-α treated group | 0 | + | 100.00 ± 6.00 | 0.0 |
| Magnoliae flos extract | 20 | + | 94.70 ± 2.82 | 16.6 |
|  | 40 | + | 74.60 ± 2.07 | 79.7 |
| Hex | 20 | + | 90.41 ± 2.36 | 30.1 |
|  | 40 | + | 78.14 ± 3.07 | 68.6 |
| CHCl₃ | 20 | + | 83.27 ± 3.06 | 52.5 |
|  | 40 | + | 68.35 ± 3.23 | 99.3 |
| BuOH | 20 | + | 89.34 ± 3.20 | 33.4 |
|  | 40 | + | 85.34 ± 2.19 | 46.0 |
| D.W. | 20 | + | 93.80 ± 3.80 | 19.4 |
|  | 40 | + | 86.43 ± 8.33 | 42.5 |

<TEST EXAMPLE 3> CYTOTOXICITY OF THE COMPOUNDS OF MAGNOLIAE FLOS IN HUMAN LUNG CANCER MUCOSA CELLS (H292)

H292 cells were inoculated on a 96-well plate and allowed to attach for 12 hours, followed by treatment with the compounds of Magnoliae flos (S1 to S7) in different concentrations and culturing for 24 hours. Then, 10 μl of the CCK-8 solution (Dojindo Laboratories, Japan) was mixed with 90 μl of the medium, and 100 μl thereof was added per well. After incubation for a minimum of 30 minutes to a maximum of 4 hours, the absorbance was measured at 570 nm. The cell viability was calculated according to the following Equation 2 with a negative control group treated with 0.2% DMSO as a reference of 100%.

As a result, as shown in the following Table 5, it was confirmed that no cytotoxicity was observed at a concentration of 20 μm or less of the Magnoliae flos compounds (see Table 5).

Cell viability=(Compound treated OD 570 nm value)×100/(Negative control group OD 570 nm value)  [Equation 2]

TABLE 5

| Sample | Concentration (μM) | Viability of H292 cells (%, average ± deviation) |
|---|---|---|
| Negative control group | 0 | 100.00 ± 2.38 |
| S1 | 2.5 | 121.27 ± 2.04 |
|  | 5 | 121.61 ± 3.75 |
|  | 10 | 118.76 ± 1.96 |
|  | 20 | 114.08 ± 0.57 |
| S2 | 2.5 | 121.81 ± 2.42 |
|  | 5 | 119.94 ± 2.81 |
|  | 10 | 118.37 ± 2.55 |
|  | 20 | 112.99 ± 4.16 |
| S3 | 2.5 | 100.55 ± 1.26 |
|  | 5 | 102.75 ± 2.89 |
|  | 10 | 101.84 ± 3.42 |
|  | 20 | 102.12 ± 2.44 |
| S4 | 2.5 | 99.81 ± 2.15 |
|  | 5 | 100.74 ± 2.84 |
|  | 10 | 99.45 ± 1.53 |
|  | 20 | 97.20 ± 1.99 |
| S5 | 2.5 | 105.83 ± 1.56 |
|  | 5 | 105.34 ± 2.92 |
|  | 10 | 104.71 ± 1.49 |
|  | 20 | 98.78 ± 1.70 |
| S6 | 2.5 | 102.36 ± 2.79 |
|  | 5 | 104.19 ± 1.21 |
|  | 10 | 101.90 ± 1.26 |
|  | 20 | 104.19 ± 1.12 |
| S7 | 2.5 | 99.91 ± 1.25 |
|  | 5 | 97.97 ± 1.38 |
|  | 10 | 96.07 ± 1.02 |
|  | 20 | 95.10 ± 0.56 |

<TEST EXAMPLE 4> INHIBITORY EFFECT OF THE COMPOUNDS OF MAGNOLIAE FLOS ON THE PRODUCTION OF THE MUC5AC PROTEIN

In order to assess the effect of preventing or treating chronic obstructive pulmonary disease (COPD), the inhibitory effect of the compounds of Magnoliae flos (S1 to S7) on the secretion of MUC5AC was confirmed by the following method.

For immunoassay of the resulting MUC5AC, the supernatant (50 uL) recovered was dispensed on to a 96-well plate and dried in a thermostat set at 50° C. It was washed with PBS supplemented with 1% BSA and reacted with an MUC5AC antibody (abcam, USA) at room temperature for 1 hour. A secondary antibody was dispensed thereto for reaction for 1 hour. It was washed again and then reacted with a 3,3',5,5'-tetramethylbenzidine peroxide solution for 20 minutes. After the reaction was stopped with a sulfuric acid solution, the degree of color development was measured at 450 nm.

As a result, as shown in the following Table 6, the amount of MUC5AC secretion increased in the group treated with TNF-α. It was confirmed that the production of MUC5AC was inhibited in a manner depending on the concentrations of the compounds of Magnoliae flos (S1, S2, S3, and S4) as compared with the group treated with TNF-α as a reference of 100% (see Table 6).

TABLE 6

| Sample | Concentration (μM) | TNF-α (20 ng/mL) | MUC5AC secretion (Relative amount to TNF-α treated group, %) | Inhibition rate (%) |
|---|---|---|---|---|
| Negative control group | 0 | − | 27.60 ± 2.59 | 72.4 |
| TNF-α treated group | 0 | + | 100.00 ± 4.18 | 0.00 |
| S1 | 2.5 | + | 91.36 ± 1.29 | 8.64 |
|  | 5 | + | 73.64 ± 1.29 | 26.36 |
|  | 10 | + | 69.80 ± 3.34 | 30.2 |
| S2 | 2.5 | + | 97.57 ± 0.78 | 2.43 |
|  | 5 | + | 81.17 ± 0.82 | 18.83 |
|  | 10 | + | 65.67 ± 0.99 | 34.33 |
| S3 | 2.5 | + | 97.50 ± 0.38 | 2.5 |
|  | 5 | + | 70.62 ± 2.94 | 29.38 |
|  | 10 | + | 61.66 ± 2.30 | 30.34 |
| S4 | 2.5 | + | 90.55 ± 2.59 | 9.45 |
|  | 5 | + | 74.24 ± 2.83 | 25.76 |
|  | 10 | + | 63.71 ± 1.27 | 36.29 |
| S5 | 2.5 | + | 86.07 ± 3.66 | 13.93 |
|  | 5 | + | 89.88 ± 0.79 | 10.12 |
|  | 10 | + | 83.57 ± 4.84 | 16.43 |
| S6 | 2.5 | + | 99.85 ± 4.50 | 0.15 |
|  | 5 | + | 95.81 ± 6.10 | 4.19 |
|  | 10 | + | 98.80 ± 5.73 | 1.2 |
| S7 | 2.5 | + | 99.21 ± 3.33 | 0.79 |
|  | 5 | + | 98.31 ± 3.72 | 1.69 |
|  | 10 | + | 88.95 ± 3.12 | 11.05 |

<TEST EXAMPLE 5> INHIBITORY EFFECT OF THE COMPOUNDS OF *MAGNOLIAE FLOS* ON THE ACTIVITY OF THE MUC5AC PROMOTERS

Based on the results of <Test Example 4> above, in order to confirm the inhibitory effect of the compounds of *Magnoliae flos* (S1 to S4) on the expression of the MUC5AC protein, the following experiment was carried out.

Specifically, H292 cells were transfected with luciferase reporter vector pGL4.14 (luc2P/MUC5AC promotor/Hygro) and cultured for 12 hours, followed by treatment with the target compounds of *Magnoliae flos* (S1 to S4, 10 μM), treatment with TNF-α (20 ng/ml), and culturing for 12 hours. The degree of activation of luciferase was confirmed using a One-glow Luciferase Assay System (Promega).

As a result, as shown in the following Table 7, the activity of the MUC5AC promoters increased in the group treated with TNF-α. It was confirmed that the activity of the MUC5AC promoters was significantly inhibited by the compounds of *Magnoliae flos* (S1 to S4) as compared with the group treated with TNF-α as a reference of 100% (see Table 7).

TABLE 7

| Sample | Concentration (μM) | TNF-α (20 ng/mL) | MUC5AC secretion (Relative amount to TNF-α treated group, %) | Inhibition rate (%) |
|---|---|---|---|---|
| Negative control group | 10 | − | 40.53 ± 5.69 | 59.47 |
| TNF-α treated group | 10 | + | 100.00 ± 10.25 | 0.00 |
| S1 | 10 | + | 44.26 ± 0.92 | 55.74 |
| S2 | 10 | + | 44.8 ± 7.33 | 55.2 |
| S3 | 10 | + | 43.73 ± 8.81 | 56.27 |
| S4 | 10 | + | 36.8 ± 6.97 | 63.2 |

<TEST EXAMPLE 6> INHIBITORY EFFECT OF FRACTION 10 AND THE COMPOUNDS OF *MAGNOLIAE FLOS* ON INFLAMMATORY CELLS OF THE CHRONIC OBSTRUCTIVE PULMONARY DISEASE (COPD) MODEL

<6-1> Preparation of an Animal Model of Chronic Obstructive Pulmonary Disease (COPD)

In order to assess the effect of Fraction 10 among the additional fractions (hereinafter referred to as an active fraction) separated in <Example 3> above and the compounds (S1 to S7) separated in <Example 5> above on the treatment of chronic obstructive pulmonary disease, an animal model of chronic obstructive pulmonary disease was prepared in the following manner.

Six-week-old male SPF (specific pathogen-free) C57BL/6N mice (22 to 24 g) were supplied by Koatech (Korea). These animals were fed with a sufficient amount of solid feed (no antibiotics, Samyang Feed Co.) and water until the day of the experiment. They were allowed to adapt for 1 week in a light-dark cycle environment at a temperature of 22±2° C. and a humidity of 55±15%, and then subjected to the experiment.

The animal model was exposed to cigarette smoke to induce chronic obstructive pulmonary disease. 3R4F Kentuchy Reference Cigarettes as standard cigarettes for use to generate cigarette smoke were supplied by University of California (USA). The standard cigarettes contain 9.4 mg of tar, 11 mg of total particle matter (TPM), and 12 mg of carbon monoxide per 1 cigarette. The standard cigarettes were used after harmonization for 48 hours to 72 hours at a temperature of 22±1° C. and a humidity of 60±2%. Further, Cigarette Smoke Generator manufactured by Korea BioLink (Korea) was used for exposure to cigarette smoke. Cigarette smoke was inhaled for 1 hour (8 pcs/hour) for 7 days from 1 hour after oral administration of a sample. 10 μg of LPS (lipopolysaccharide) in PBS 50 μL was injected intranasally to each mouse on the 4$^{th}$ day of the experiment after the mouse was anesthetized with zoletyl 1 hour before the exposure to cigarette smoke. The smoking condition was 8 puffs per 1 standard cigarette (volume: 45 mL, duration: 2 seconds, and interval: 1 time/min).

<6-2> Treatment of the Animal Model of Chronic Obstructive Pulmonary Disease (COPD) with the Active Fraction and the Compounds of *Magnoliae flos*

The active fraction of *Magnoliae flos* (15, 30 mg/kg) and roflumilast (10 mg/kg) as therapeutic substances were dissolved in 0.5% sodium carboxymethyl cellulose and were orally administered 1 hour before the exposure to cigarette smoke.

The experimental groups were divided into (i) normal control (NC) group; (ii) cigarette smoke+LPS exposure group (COPD); (iii) experimental group administered with roflumilast (ROF) (10 mg/kg, p.o) 1 hour before the exposure to cigarette smoke+LPS; and (iv) experimental group administered with the active fraction of *Magnoliae flos* (15, 30 mg/kg, p.o; *Magnoliae flos* 15 and *Magnoliae flos* 30) 1 hour before the exposure to cigarette smoke+LPS. In addition, the compounds S1, S2, S3, and S4 each were dissolved in PBS containing 10% of ethanol, and the compounds S5, S6, and S7 were dissolved in PBS containing 10% of DMSO (dimethyl sulfoxide). Then, they were administered in the same manner as above.

<6-3> Separation of the Bronchoalveolar Lavage Fluid (BALF) and the Effect on the Reduction of Inflammatory Cells The bronchial alveolar lavage fluid was separated from the animal model treated with the active fraction and the compounds of *Magnoliae flos* in <Test Example 6-2> above in the following manner, and the number of inflammatory cells was measured.

Specifically, a mouse sonde was inserted into the bronchial tube, a 1 mL syringe containing 0.7 mL of DPBS (Dulbecco's Phosphate-Buffered Saline) was connected thereto, and DPBS was injected into the lung. The injected DPBS was recovered, and this procedure was repeated twice. The bronchoalveolar lavage fluid separated by DPBS was centrifuged at 1,500 rpm for 15 minutes to make a cell pellet. The supernatant was stored frozen at −70° C. for cytokine analysis. Each cell obtained was suspended in DPBS, attached to a slide glass using a cytospin centrifuge, and Diff-Quik stained. The number of inflammatory cells in each sample was counted through microscopic examination, and the inhibition rate was calculated according to the following Equation 3.

As a result, as shown in the following Table 8, the number of inflammatory cells in the bronchoalveolar lavage fluid decreased in the group treated with the active fraction of *Magnoliae flos* as compared with the COPD-induced group, and the number of neutrophils was inhibited by 21.1% in the 15 mg/kg administration group and by 54.4% in the 30 mg/kg administration group as compared with the COPD-induced group.

In addition, the increase in inflammatory cells was effectively inhibited in the group administered with the *Magno-* liae flos compounds as compared with the COPD-induced group, especially in the groups treated with 51, S3, S6, and S7 (see Table 8).

Inhibition rate=(Value of COPD-induced group−
value of target substance administered group)×
100/(Value of COPD-induced group)    [Equation 3]

TABLE 8

| Inhibition rate of inflammatory cell infiltration (%) | | | |
|---|---|---|---|
| Experimental group | Neutrophil | Macrophage | Total inflammatory cells |
| ROF (10 mg/kg) | 37.4 ± 8.3 | 30.6 ± 9.9 | 39.4 ± 7.2 |
| Active fraction of Magnoliae flos (15 mg/kg) | 21.1 | 43.7 | 32.4 |
| Active fraction of Magnoliae flos (30 mg/kg) | 54.4 | 59.6 | 58.0 |
| S1-15 | 45.9 ± 3.4 | 12.8 ± 10.4 | 42.2 ± 2.5 |
| S1-30 | 54.5 ± 3.4 | 40.0 ± 5.4 | 54.3 ± 3.5 |
| S2-15 | 47.2 ± 3.6 | 21.6 ± 6.3 | 44.7 ± 3.9 |
| S2-30 | 31.0 ± 7.1 | 10.7 ± 9.8 | 30.7 ± 5.3 |
| S3-15 | 17.9 ± 6.6 | 19.4 ± 5.4 | 23.3 ± 5.5 |
| S3-30 | 42.1 ± 3.9 | 33.2 ± 6.2 | 43.5 ± 3.4 |
| S4-15 | 13.8 ± 4.9 | 0.0 ± 0.0 | 14.0 ± 5.1 |
| S4-30 | 25.7 ± 5.5 | 21.4 ± 6.5 | 29.1 ± 4.4 |
| Inhibition rate of inflammatory cell infiltration (%) | | | |
| ROF (10 mg/kg) | 31.9 ± 7.6 | 36.9 ± 15.0 | 34.9 ± 4.6 |
| S5-15 | 44.2 ± 4.1 | 28.3 ± 7.2 | 33.0 ± 4.4 |
| S5-30 | 53.2 ± 5.4 | 37.1 ± 7.1 | 43.2 ± 5.4 |
| S6-15 | 50.7 ± 5.9 | 37.8 ± 5.3 | 42.8 ± 2.4 |
| S6-30 | 66.3 ± 5.9 | 26.0 ± 5.6 | 43.7 ± 4.7 |
| S7-15 | 51.7 ± 6.3 | 37.1 ± 2.8 | 44.1 ± 3.7 |
| S7-30 | 38.2 ± 5.4 | 34.8 ± 6.1 | 34.1 ± 6.1 |

<TEST EXAMPLE 7> INHIBITORY EFFECT OF MAGNOLIAE FLOS ON INFLAMMATORY CELLS IN THE BRONCHOALVEOLAR LAVAGE FLUID OF THE CHRONIC OBSTRUCTIVE PULMONARY DISEASE (COPD) MODEL

Production of active oxygen species in the bronchoalveolar lavage fluid obtained in <Test Example 6-3> above was confirmed by the following method.

Specifically, the separated BALF (200 μL) was treated to the final concentration of 20 μM of DCF-DA (dihydrodichlorofluorescein diacetate, Sigma-Aldrich, USA), followed by culturing for 30 minutes and measurement using Fluorescence (Molecular Device, USA). The inhibition rate was calculated by Equation 3 above.

As a result, as shown in the following Table 9, the production of reactive oxygen species increased significantly in the COPD-induced group as compared with the normal group, whereas the production of reactive oxygen species decreased in the group administered with the Magnoliae flos active fraction as compared with the COPD-induced group—inhibited by 17.2% in the 15 mg/kg administered group and by 33.0% in the 30 mg/kg administered group.

In addition, the production of active oxygen species was also inhibited in the groups administered with the compounds of Magnoliae flos (S1 to S7). In particular, the groups administered with S1, S3, S5, and S6 showed relatively higher inhibition rates in a manner depending on concentration than those of the groups administered with other substances. The S7 administered group showed a higher inhibition rate in the low dose groups (see Table 9).

TABLE 9

| Experimental group | Active oxygen inhibition rate (%) |
|---|---|
| ROF (10 mg/kg) | 25.9 ± 4.3 |
| Active fraction of Magnoliae flos (15 mg/kg) | 17.2 |
| Active fraction of Magnoliae flos (30 mg/kg) | 33.0 |
| S1-15 | 17.9 ± 5.1 |
| S1-30 | 34.7 ± 3.2 |
| S2-15 | 21.8 ± 4.4 |
| S2-30 | 14.0 ± 8.3 |
| S3-15 | 15.1 ± 4.7 |
| S3-30 | 32.5 ± 3.1 |
| S4-15 | 13.5 ± 4.3 |
| S4-30 | 15.9 ± 4.2 |
| S5-15 | 31.3 ± 2.5 |
| S5-30 | 39.7 ± 3.5 |
| S6-15 | 30.6 ± 7.6 |
| S6-30 | 33.5 ± 6.9 |
| S7-15 | 47.5 ± 5.2 |
| S7-30 | 39.6 ± 6.9 |

<TEST EXAMPLE 8> EFFECT OF MAGNOLIAE FLOS ON THE REDUCTION OF CYTOKINES IN THE BRONCHOALVEOLAR LAVAGE FLUID OF THE CHRONIC OBSTRUCTIVE PULMONARY DISEASE (COPD) MODEL

Cytokines were measured in the cell supernatant obtained in <Test Example 6-3> above by the following method.

Specifically, the levels of IL-6 (R & D System, USA) and TNF-α (BD Bioscience, USA) in the separated BALF were measured by enzyme-linked immuno-sorbent assay (ELISA). Each cytokine analysis was carried out according to the manufacturer's test method. The absorbance was measured at 450 nm with an ELISA leader (Molecular Devices, USA), and the inhibition rate was measured using Equation 3 above.

As a result, as shown in the following Table 10, IL-6 in the bronchoalveolar lavage fluid significantly increased in the COPD-induced group as compared with the normal group, whereas IL-6 in the bronchoalveolar lavage fluid decreased in the group administered with roflumilast and the group administered with the Magnoliae flos active fraction as compared with the COPD-induced group. In particular, in the case of the groups administered with the active fraction of Magnoliae flos, IL-6 was reduced by 26.0% in the 15 mg/kg administered group and by 41.3% in the 30 mg/kg to administered group as compared with the COPD-induced group. Also, in the case of TNF-α, 28.8% was reduced in the 15 mg/kg administered group, and 33.4% was reduced in the 30 mg/kg administered group in the groups administered with the active fraction of Magnoliae flos as compared with the COPD-induced group.

In addition, the secretion of IL-6 and TNF-α was inhibited in the groups administered with the compounds of Magnoliae flos (S1 to S7). A concentration-dependent decrease of IL-6 secretion was observed in the groups administered with S1, S4, S5, and S6, and a concentration-dependent inhibition was observed in the groups administered with 51, S3, S4, S5, and S6 in the case of TNF-α (see Table 10).

TABLE 10

| Experimental group | IL-6 inhibition rate (%) | TNF-α inhibition rate (%) |
| --- | --- | --- |
| ROF (10 mg/kg) | 20.8 ± 5.0 | 30.8 ± 5.9 |
| Active fraction of *Magnoliae flos* (15 mg/kg) | 26.0 | 28.8 |
| Active fraction of *Magnoliae flos* (30 mg/kg) | 41.3 | 33.4 |
| S1-15 | 56.2 ± 6.6 | 25.0 ± 7.8 |
| S1-30 | 67.6 ± 6.6 | 38.0 ± 4.1 |
| S2-15 | 64.9 ± 4.8 | 29.2 ± 4.8 |
| S2-30 | 36.6 ± 8.9 | 31.0 ± 7.2 |
| S3-15 | 45.9 ± 6.2 | 26.7 ± 7.0 |
| S3-30 | 43.9 ± 6.5 | 41.7 ± 4.4 |
| S4-15 | 0.0 ± 0.0 | 13.8 ± 5.5 |
| S4-30 | 40.3 ± 3.7 | 24.7 ± 6.5 |
| ROF | 50.2 ± 6.2 | 44.8 ± 3.8 |
| S5-15 | 36.1 ± 5.5 | 32.9 ± 4.8 |
| S5-30 | 48.8 ± 4.4 | 39.1 ± 1.9 |
| S6-15 | 59.3 ± 7.2 | 39.8 ± 10.2 |
| S6-30 | 62.9 ± 6.0 | 47.8 ± 4.7 |
| S7-15 | 50.8 ± 17.0 | 49.1 ± 2.6 |
| S7-30 | 31.4 ± 9.6 | 34.1 ± 7.1 |

<TEST EXAMPLE 9> INHIBITORY EFFECT OF *MAGNOLIAE FLOS* ON INFLAMMATION IN THE LUNG TISSUE OF THE COPD MODEL

The inhibitory effect of the active fraction and the compounds (S1 to S7) of *Magnoliae flos* on inflammation in the lung tissue in the COPD model of <Test Example 6-2> above was confirmed by the following method.

Specifically, the lung was taken out and immediately fixed in a 10% formaldehyde solution, which was then sliced and washed with running water for 8 hours. It was then embedded in epoxy and Hematoxylin & Eosin stained, and the pathological changes in the lung tissue were examined using an optical microscope.

As a result, as shown in FIGS. 5a-5c, extensive infiltration of inflammatory cells around the alveoli and bronchi in the COPD-induced group was observed as compared with the normal group. In contrast, such infiltration of inflammatory cells was reduced in the group administered with roflumilast, and the infiltration of inflammatory cells was also reduced in the groups administered with the active fraction and the compounds of *Magnoliae flos* as compared with the COPD-induced group. This decrease in the infiltration of inflammatory cells was significantly observed in the group administered with 30 mg/kg of the *Magnoliae flos* active fraction (see FIGS. 5a-5c).

The invention claimed is:

1. A method for treating chronic obstructive pulmonary disease in a subject in need thereof, which comprises administering a pharmaceutically effective amount of (i) an extract of *Magnoliae flo*, (ii) an active fraction obtained by fractionation of the extract of *Magnoliae flos* with an organic solvent, or (iii) a combination of (i) and (ii) to the subject.

2. The method according to claim 1, wherein the extract of *Magnoliae flos* is obtained by extracting *Magnoliae flos* using an extraction solvent of water, a $C_1$ to $C_2$ lower alcohol, or a mixture thereof.

3. The method according to claim 1, wherein the organic solvent is hexane or chloroform.

4. The method according to claim 1, wherein the extract of (i) is a hexane fraction, a chloroform fraction, or a water fraction obtained by sequentially fractionating the extract of *Magnoliae flos* of (i) with hexane, chloroform, and water, in this order.

5. The method according to claim 1, wherein the active fraction of (ii) is obtained by fractionating the extract *Magnoliae flos* of (i) with a mixed solvent of hexane and ethyl acetate.

6. The method according to claim 1, wherein (i) the extract of *Magnoliae flos*, (ii) the active fraction obtained by fractionation of the extract of *Magnoliae flos* with an organic solvent, and (iii) the combination the (i) and (ii) each comprise a compound of the following Formula 1, a stereoisomer thereof, or a pharmaceutically acceptable salt thereof as an active ingredient:

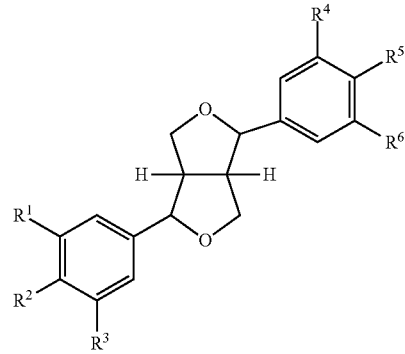

Formula 1 wherein, in Formula 1 above, $R^1$, $R^4$, $R^5$, and $R^6$ are independently $C_{1-3}$ straight or branched chain alkyl, $C_{1-3}$ straight or branched chain alkoxy, or hydrogen; and $R^2$ and $R^3$ are independently $C_{1-3}$ straight or branched chain alkyl, $C_{1-3}$ straight or branched chain alkoxy, or hydrogen, or $R^2$ and $R^3$ may together form

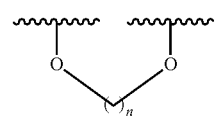

wherein n is an integer of 1 to 3.

7. The method according to claim 6, wherein $R^1$, $R^4$, $R^5$, and $R^6$ are independently $C_{1-3}$ straight or branched chain alkoxy or hydrogen; and $R^2$ and $R^3$ are independently $C_{1-3}$ straight or branched chain alkoxy or hydrogen, or $R^2$ and $R^3$ may together form

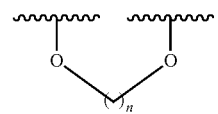

wherein n is an integer of 1 to 2.

8. The method according to claim 6, wherein $R^1$, $R^4$, $R^5$, and $R^6$ are independently methoxy or hydrogen; and $R^2$ and $R^3$ are independently methoxy or hydrogen, or $R^2$ and $R^3$ may together form

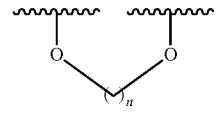

wherein n is 1.

9. The method according to claim 6, wherein the compound of Formula 1 is a compound of any one of the following Formulae 2 to 8:

Formula 2
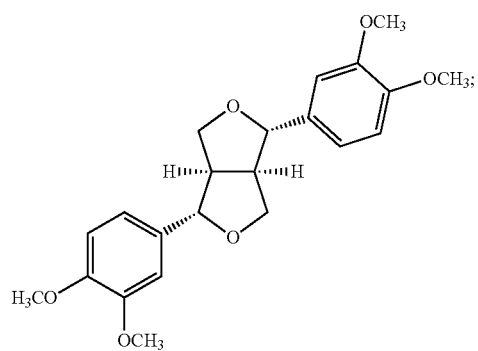
Formula 3
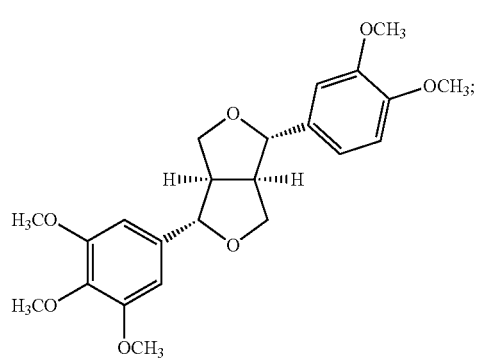
Formula 4
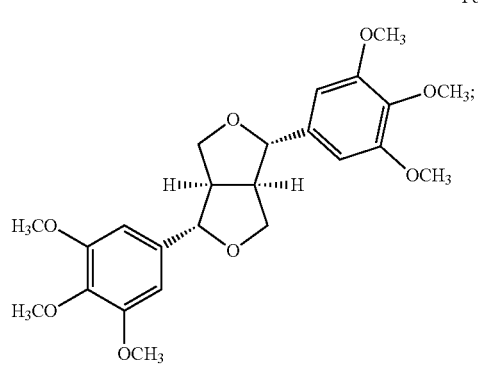
Formula 5
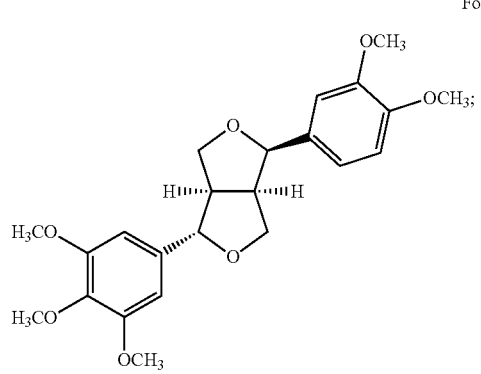
Formula 6
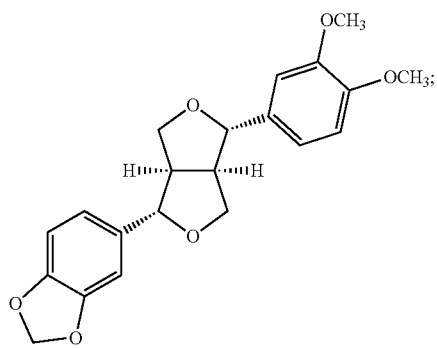
Formula 7
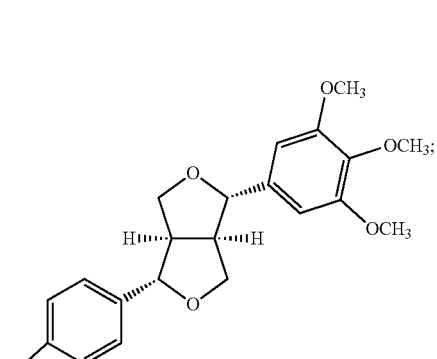
Formula 8
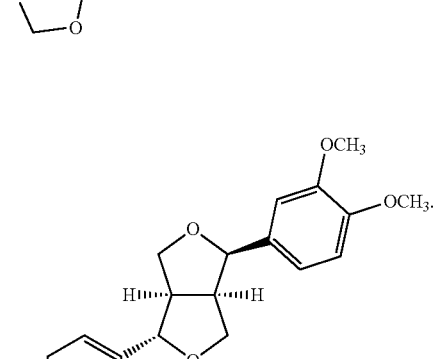
10. The method according to claim 1, wherein the extract of (i), or the active fraction of (ii), or the combination of (iii) is in a pharmaceutically acceptable carrier, an excipient or a diluent.
11. The method according to claim 5, wherein the ratio of the hexane to the ethyl acetate in the mixed solvent is 3:1 by volume.
* * * * *